United States Patent
Ashkenazi et al.

(10) Patent No.: US 7,855,066 B1
(45) Date of Patent: Dec. 21, 2010

(54) METHODS FOR MAKING APO-2 LIGAND USING DIVALENT METAL IONS

(75) Inventors: Avi J. Ashkenazi, San Mateo, CA (US); Sarah Hymowitz, San Francisco, CA (US); Robert F. Kelley, San Bruno, CA (US); Iphigenia Koumenis, Winston-Salem, NC (US); Woon-Lam Susan Leung, San Mateo, CA (US); Mark O'Connell, Montara, CA (US); Roger Pai, Los Altos, CA (US); Zahra Shahrokh, Weston, MA (US); Laura Simmons, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 484 days.

(21) Appl. No.: 11/528,948

(22) Filed: Sep. 28, 2006

Related U.S. Application Data

(63) Continuation of application No. 09/603,866, filed on Jun. 26, 2000, now abandoned.

(60) Provisional application No. 60/141,342, filed on Jun. 28, 1999.

(51) Int. Cl.
*C12N 5/10* (2006.01)
*C12N 15/12* (2006.01)
*C07K 14/52* (2006.01)

(52) U.S. Cl. .................. 435/252.33; 530/350; 435/69.1; 435/320.1

(58) Field of Classification Search .................. None
See application file for complete search history.

(56) References Cited

U.S. PATENT DOCUMENTS

| 5,763,223 | A | * | 6/1998 | Wiley et al. |
| 5,863,760 | A | * | 1/1999 | Light et al. |
| 6,387,650 | B1 | * | 5/2002 | Townsend et al. |

FOREIGN PATENT DOCUMENTS

| EP | 417563 | 3/1991 |
| WO | WO 92/03478 | 3/1992 |
| WO | WO 92/17200 | 10/1992 |
| WO | WO 97/01633 | 1/1997 |
| WO | WO 97/23615 | 7/1997 |
| WO | WO 97/25428 | 7/1997 |
| WO | WO 97/33899 | 9/1997 |

(Continued)

OTHER PUBLICATIONS

Hymowitz et al., A unique zinc-binding site revealed by a high-resolution X-ray structure of homotrimeric Apo2L/TRAIL, Biochem. 39:633-640, 2000.*

(Continued)

*Primary Examiner*—Lorraine Spector
*Assistant Examiner*—Claire Kaufman
(74) *Attorney, Agent, or Firm*—Diane L. Marschang

(57) ABSTRACT

Methods of making Apo-2 ligand and formulations of Apo-2 ligand using divalent metal ions are provided. Such divalent metal ions include zinc and cobalt which improve Apo-2 ligand trimer formation and stability. The crystal structure of Apo-2 ligand is also provided, along with Apo-2 ligand variant polypeptides identified using oligonucleotide-directed mutagenesis.

8 Claims, 12 Drawing Sheets

FOREIGN PATENT DOCUMENTS

| WO | WO 97/46686 | 12/1997 |
|----|-------------|---------|
| WO | WO 98/14577 | 4/1998 |
| WO | 98/51793 | 11/1998 |
| WO | WO 99/10484 | 3/1999 |
| WO | WO 99/36535 | 7/1999 |
| WO | WO 00/02900 | 1/2000 |
| WO | WO 01/18041 | 3/2001 |
| WO | WO 01/18055 | 3/2001 |

OTHER PUBLICATIONS

Sambrook et al., Molecular Cloning, Cold Spring Harbor Laboratory Press (USA), 2nd Ed., pp. A.2-A.3, 1989.*
Kim et al., Overexpression of archaeal proteins in *Escherichia coli*, Biochem. Lett. 20(3):207-210, Mar. 1998.*
RPMI-1640 Medium Formulation, Catalogue No. 30-2001, American Type Culture Collection, 2002.*
New Brunswick Scientific, *E. coli* Fermentation Using a BioFlo 100 Bench-Top Fermentor, (Edison NJ, USA) pp. 1-4, 2007.*
J.M. Scientific, Economic fermentor and bioreactor, Laboratorytalk (online publication), Jul. 28, 2003.*
Beck et al., Expression of human placental alkaline phosphatase in *Escherichia coli*, Protein Exp. Purif. 5(2):192-197, Apr. 1994, abstract only.*
Ratledge et al., Effect of iron and zinc on growht patterns of *Escherichia coli* in an iron-deficient medium, J. Bact. 87(4):823-827, Apr. 1964.*
Darnell et al., Molecular Cell Biology, Scientific American Books:New York, 1986.*
Wikipedia online encyclopedia, Lysogeny Broth, Jun. 9, 2009, accessed Jun. 2009.*
Armitage et al., "Molecular and Biological Characterization of a Murine Ligand for CD40" *Nature* 357(6373):80-82 (1992).
Aruffo et al., "CD44 is the Principal Cell Surface Receptor for Hyaluronate" *Cell* 61:1303-1313 (Jun. 29, 1990).
Ashkenazi and Dixit., "Death Receptors: Signaling and Modulation." *Science.* 281(5381):1305-1308 (1998).
Ashkenazi et al., "Protection Against Endotoxic Shock by a Tumor Necrosis Factor Receptor Immunoadhesin" *Proc. Natl. Acad. Sci.* 88:10535-10539 (Dec. 1991).
Banner et al., "Crystal Structure of the Soluble Human 55 kd TNF Receptor-Human TNFβ Complex: Implications for TNF Receptor Activation" *Cell* 73:431-445 (1993).
Barr and Tomei, "Apoptosis and Its Role in Human Disease" *Bio/Technology* 12:487-493 (1994).
Bodmer et al., "TRAMP, A Novel Apoptosis-Mediating Receptor with Sequence Homology to Tumor Necrosis Factor Receptor 1 and Fas(Apo-1/CD95)." *Immunity.* 6:79-88 (1997).
Brockhaus et al., "Identification of Two Types of Tumor Necrosis Factor Receptors on Human Cell Lines by Monoclonal Antibodies." *Proc. Natl. Acad. Sci. USA* 87:3127-3131 (1990).
Brojatsch et al., "CAR1, A TNFR-Related Protein, Is a Cellular Receptor for Cytopathic Avian Leukosis-Sarcoma Viruses and Mediates Apoptosis." *Cell.* 87:845-855 (1996).
Browning et al., "Lymphotoxin β, a Novel Member of the TNF Family That Forms a Heteromeric Complex with Lymphotoxin on the Cell Surface" *Cell* 72:847-856 (1993).
Cha et al., "2.8 A Resolution Crystal Structure of Human TRAIL, a Cytokine with Selective Antitumor Activity" *Immunity* 11:253-261 (1999).
Cha et al., "Crystal Structure of TRAIL-DR5 Complex Identifies a Critical Role of the Unique Frame Insertion in Conferring Recognition Specificity" *The Journal of Biological Chemistry*, JBC Papers in Press vol. 275 (40) :31171-31177 (Jul. 11, 2000).
Cha et al., "Expression, purification and crystallization of-recombinant human TRAIL" *Acta Chrystallographica, Section D: Biological Chrystallography* 55:1101-1104 (1999).
Chang et al., "High-Level Secretion of Human Growth Hormone by *Escherichia coli*" *Gene* 55:189-196 (1987).
Chicheportiche et al., "TWEAK, A New Secreted Ligand in the tumor Necrosis Factor Family that Weakly Induces Apoptosis" *Journal of Biological Chemistry* 272(51):32401-32410 (1997).
Chinnaiyan et al., "Signal Transduction by DR3, A Death Domain-Containing Receptor Related to TNFR-1 and CD95." *Science.* 274:990-992 (1996).
Christianson, D., "Structural Biology of Zinc" *Advances in Protein Chemistry* 42:281-355 (1991).
DeBoer et al., "Construction of a Tandem trp-lac Promoter and a Hybrid trp-lac Promoter for Efficient and Controlled Expression of the Human Growth Hormone Gene in *Escherichia coli*" *Promoters: Structure and Function*, New York: Praeger pp. 462-481 (1982).
Degli-Esposti et al., "Cloning and Characterization of TRAIL-R3, a Novel Member of the Emerging TRAIL Receptor Family" *Journal of Experimental Medicine* 186(7):1165-1170 (1997).
Degli-Esposti et al., "The Novel Receptor TRAIL-R4 Induces Nf-κB and Protects against TRAIL-Mediated Apoptosis, yet Retains an Incomplete Death Domain" *Immunity* 7 :813-820 (1997).
Feese et al, "Cation-promoted association of a regulatory and target protein is controlled by protein phosphorylation" *Proc. Natl. Acad.* 91:3544-3548 (1994).
Garcia et al., "The *E. coli* dnaY Gene Encodes an Arginine Transfer RNA." *Cell.* 45:453-459 (1986).
Golstein, P., "Cell Death: TRAIL and its Receptors" *Curr. Biol* 7:R750-R753 (1997).
Goodwin et al., "Molecular Cloning and Expression of the Type 1 and Type 2 Murine Receptors for Tumor Necrosis Factor." *Mol. Cell. Bio.* 11:3020-3026 (1991).
Gruss and Dower, "Tumor Necrosis Factor Ligand Superfamily: Involvement in the Pathology of Malignant Lymphomas" *Blood* 85:3378-3404 (1995).
Hale et al., "Demonstration of In Vitro and In Vivo Efficacy of Two Biologically Active Human Soluble TNF Receptors Expressed in *E. coli.*" *J. Cell. Biochem.* (abstract only, suppl. 15F; P 424) pp. 113 (1991).
Hohmann et al., "Two different cell types have different major receptors for human tumor necrosis factor (TNFα)" *Journal of Biological Chemistry* 264 (25):14927-14934 (1989).
Hymowitz et al., "A unique zinc-binding site revealed by the high-resolution X-ray structure of homotrimeric Apo2L/TRAIL" *Biochemistry* 39(4):633-640 (2000).
Hymowitz et al., "Triggering Cell Death: The Crystal Structure of Apo2L/TRAIL in a complex with Death Receptor 5" *Molecular Cell* 4(4):563-571 (1999).
Itoh et al., "The Polypeptide Encoded by the cDNA for Human Cell Surface Antigen Fas Can Mediate Apoptosis." *Cell.* 66:233-243 (1991).
Johnson et al., "Expression and Structure of the Human NGF Receptor" *Cell* 47:545-554 (1986).
Karpusas et al., "The crystal structure of human interferon β at 2.2-A resolution" *Proc. Natl. Acad. Sci.* 94:11813-11818 (1997).
Kitson et al., "A Death-Domain-Containing Receptor that Mediates Apoptosis" *Nature* 384:372-375 (1996).
Kohno et al., "A Second Tumor Necrosis Factor Receptor Gene Product Can Shed a Naturally Occurring Tumor Necrosis Factor Inhibitor." *Proc. Natl. Acad. Sci. USA* 87:8331-8335 (1990).
Komine et al., "Genomic Organization and Physical Mapping of the Transfer RNA Genes in *Escherichia coli* K12" *J. Mol. Biol.* 212:579-598 (1990).
Kunkel et al., "Rapid and Efficient Site-specific Mutagenesis Without Phenotypic Selection" *Methods in Enzymology* 154:367-382 (1987).
Kunkel, T., "Rapid and Efficient Site-Specific Mutagenesis Without Phenotypic Selection" *Proc. Natl. Acad. Sci.* 82(2):488-492 (Jan. 1985).
Lawrence et al., "Differential hepatocyte toxicity of recombinant Apo2L/TRAIL versions" *Nature Medicine* 7(4):383-385 (Apr. 2001).
Lewis et al., "Cloning and Expression of cDNAs for Two Distinct Murine Tumor Necrosis Factor Receptors Demonstrate One Receptor is Species Specific." *PNAS USA.* 88:2830-2834 (1991).
Loetscher et al., "Molecular Cloning and Expression of the Human 55 kd Tumor Necrosis Factor Receptor" *Cell* 61:351-359 (1990).

MacFarlane et al., "Identification and Molecular Cloning of Two Novel Receptors for the Cytotoxic Ligand TRAIL" *Journal of Biological Chemistry* 272(41):25417-25420 (1997).
Mallett et al., "Characterization of the MRC OX40 Antigen of Activated CD4 Positive T Lymphocytes—a Molecule Related to Nerve Growth Factor Receptor" *EMBO Journal* 9:1063-1068 (1990).
Marsters et al., "A Novel Receptor for Apo2L/TRAIL Contains a Truncated Death Domain" *Current Biology* 7:1003-1006 (1997).
Marsters et al., "Activation of Apoptosis by Apo-2 Ligand is Independent of FADD but Blocked by CrmA." *Current Biology*. 6(6):750-752 (1996).
Marsters et al., "Apo-3, A New Member of the Tumor Necrosis Factor Receptor Family, Contains a Death Domain and Activates Apoptosis and NF-κB." *Curr. Biol.* 6(12):1669-1676 (1996).
Marsters et al., "Herpesvirus Entry Mediator, A Member of the Tumor Necrosis Factor Receptor (TNFR) Family, Interacts with Members of the TNFR-Associated Factor Family and Activates the Transcription Factors NF-κB and AP-1." *J. Bio. Chem.* 272(22):14029-14032 (1997).
Marsters et al., "Identification of a Ligand for the Death-Domain-Containing Receptor Apo3" *Current Biology* 8(9):525-528 (1998).
Mongkolsapaya et al., "Cutting Edge: Lymphocyte Inhibitor of TRAIL (TNF-Related Apoptosis-Inducing Ligand) : A New Receptor Protecting Lymphocytes From the Death Ligand TRAIL" *J. Immunol.* 160(1):3-6 (1998).
Mongkolsapaya et al., "Structure of the Trail-DR5 complex reveals mechanisms conferring specificity in apoptotic initiation" *Nature Structural Biology* 6(11):1048-1053 (Nov. 1999).
Montgomery et al., "Herpes Simplex Virus-1 Entry into Cells Mediated by a Novel Member of the TNF/NGF Receptor Family" *Cell* 87(3):427-436 (1996).
Nocentini et al., "A New Member of the Tumor Necrosis Factor/Nerve Growth Factor Receptor Family Inhibits T Cell Receptor-Induced Apoptosis." *Proc. Natl. Acad. Sci.* 94(12):6216-6221 (1997).
Nophar et al., "Soluble Forms of Tumor Necrosis Factor Receptors (TNF-Rs). The cDNA for the Type I TNF-R, Cloned Using Amino Acid Sequence Data of its Soluble Form, Encodes Both the Cell Surface and a Soluble Form of the Receptor." *Embo Journal.* 9 :3269-3278 (1990).
Otwinowski and Minor, "Processing of X-ray Diffraction Data Collected in Oscillation Mode" *Methods in Enzymology*, Carter and Sweet, San Diego, CA:Academic Press vol. 276 :307-326 (1997).
Otwinowski et al. *Proceedings of the CCP4 Study Weekend: Data Collection and Processing*, Sawyer et al., Daresbury, England :Daresbury Laboratory pp. 56-62 (1993).
Pan et al., "An Antagonist Decoy Receptor and a Death-Domain Containing Receptor for TRAIL" *Science* 277:815-818 (Aug. 1997).
Pan et al., "Identification and Functional Characterization of DR6, A Novel Death Domain-Containing TNF Receptor." *Febs Letters.* 431(3):351-356 (1998).
Pan et al., "The Receptor for the Cytotoxic Ligand TRAIL" *Science* 276:111-113 (Apr. 4, 1997).
Pan et al., "TRUNDD, A New Member of the TRAIL Receptor Family That Antagonizes TRAIL Signalling" *FEBS Letters* 424(1-2):41-45 (1998).
Peetre et al., "A tumor necrosis factor binding protein is present in human biological fluids" *European Journal of Haematology* 41:414-419 (1988).
Pitti et al., "Genomic Amplification of a Decoy Receptor for Fas Ligand in Lung and Colon Cancer" *Nature* 396(6712):699-703 (Dec. 17, 1998).
Pitti et al., "Induction of Apoptosis by Apo-2 Ligand, a New Member of the Tumor Necrosis Factor Cytokine Family" *Journal of Biological Chemistry* 271:12687-12690 (1996).
Qin et al., "Avoiding premature apoptosis of normal epidermal cells" *Nature Medicine* 7(4):385-386 (Apr. 2001).
Radeke et al., "Gene Transfer and Molecular Cloning of the Rat Nerve Growth Factor Receptor." *Nature*. 325:593-597 (1987).
Radhakrishnan et al., "Zinc mediated dimer of human interferon-$\alpha_{2b}$ revealed by X-ray crystallography" *Structure* 4:1453-1463 (1996).
Raman et al., "Crystal Structure of Constitutive Endothelial Nitric Oxide Synthase: A Paradigm for Pterin Function Involving a Novel Metal Center" *Cell* 95:939-950 (1998).
Schall et al., "Molecular Cloning and Expression of a Receptor for Human Tumor Necrosis Factor" *Cell* 61:361-370 (1990).
Schneider et al., "Characterization of Two Receptors for TRAIL" *FEBS Letters* 416:329-334 (1997).
Scholtissek and Grosse, "A Cloning Cartridge of λ $t_o$ Terminator" *Nucl. Acids Res.* 15(7):3185 (1987).
Screaton et al., "LARD: A New Lymphoid-Specific Death Domain Containing Receptor Regulated by Alternative Pre-mRNA Splicing." *Proc. Natl. Acad. Sci.* 94:4615-4619 (1997).
Screaton et al., "TRICK2, A New Alternatively Spliced Receptor that Transduces the Cytotoxic Signal From TRAIL" *Current Biology* 7:693-696 (1997).
Seckinger et al., "Purification and biologic characterization of a specific tumor necrosis factor α Inhibitor" *Journal of Biological Chemistry* 264:11966-11973 (1989).
Sheldrick et al., "SHELXL: High-Resolution Refinement" *Methods in Enzymology*, San Diego:Academic Press vol. 277:319-343 (1997).
Sheridan et al., "Control of TRAIL-Induced Apoptosis by a Family of Signaling and Decoy Receptors" *Science* 277:818-821 (1997).
Simonet et al., "Osteoprotegerin: A Novel Secreted Protein Involved in the Regulation of Bone Density" *Cell* 89:309-319 (1997).
Smith et al., "A Receptor for Tumor Necrosis Factor Defines an Unusual Family of Cellular and Viral Proteins" *Science* 248:1019-1023 (1990).
Smith et al., "T2 Open Reading Frame From the Shope Fibroma Virus Encodes a Soluble Form of the TNF Receptor." *Biochem. & Biophys. Res. Comm.* 176:335-342 (1991).
Somers et al., "The X-ray structure of a growth hormone-prolactin receptor complex" *Nature* 372:478-481 (1994).
Stamenkovic et al., "A B-Lymphocyte Activation Molecule Related to the Nerve Growth Factor Receptor and Induced by Cytokines in Carcinomas." *EMBO Journal.* 8(5):1403-1410 (1989).
Steller, H., "Mechanisms and Genes of Cellular Suicide" *Science* 267:1445-1449 (1995).
Sutcliffe, J., "Complete Nucleotide Sequence of the *Escherichia coli* Plasmid pBR322" *Cold Spring Harbor Symposia on Quantitative Biology* 43:77-90 (1979).
Takao et al., "Novel DNA Polymorphism in the Mouse Tumor Necrosis Factor Receptors Type 1 and Type 2" *Immunogenetics* 37:199-203 (1993).
Upton et al., "Myxoma Virus Expresses a Secreted Protein with Homology to the Tumor Necrosis Factor Receptor Gene Family that Contributes to Viral Virulence." *Virology*. 184:370-382 (1991).
Upton et al., "Tumorigenic Poxviruses: Genomic Organization and DNA Sequence of the Telomeric Region of the Shope Fibroma Virus Genome." *Virology*. 160:20-30 (1987).
Walczak et al., "TRAIL-R2: A Novel Apoptosis-Mediating Receptor for TRAIL" *EMBO Journal* 16(17):5386-5397 (1997).
Welcher et al., "Nerve growth factor binding domain of the nerve growth factor receptor" *Proc. Natl. Acad. Sci. USA* 88:159-163 (1991).
Wiley et al., "Identification and Characterization of a New Member of the TNF Family that Induces Apoptosis" *Immunity* 3:673-682 (1995).
Wu et al., "Killer/DR5 is a DNA Damage-Inducible p53-Regulated Death Receptor Gene" *Nature Genetics* 17:141-143 (1997).
Yan and Chao, "Disruption of Cysteine-rich repeats of the p75 nerve growth factor receptor leads to loss of ligand binding" *Journal of Biological Chemistry* 266:12099-12104 (1991).
Yonehara et al., "A Cell-Killing Monoclonal Antibody (Anti-Fas) to a Cell Surface Antigen Co-Downregulated with the Receptor of Tumor Necrosis Factor." *Journal of Experimental Medicine* 169:1747-1756 (1989).
Kayagaki, "Metalloproteinase-mediated Release of Human Fas Ligand" *Journal of Experimental Medicine* 182:1777-1783 (1995).
McGeehan, "Regulation of tumor necrosis factor-alpha processing by a metalloproteinase inhibitor" *Nature* 370:558-61 (1994).
Schneider, "Conversion of Membrane-bound Fas (CD95) Ligand to Its Soluble Form is Associated with Downregulation of Its Proapoptotic Activity and Loss of Liver Toxicity" *Journal of Experimental Medicine* 187(8):1205-1213 (1998).

* cited by examiner

```
  1  TTTCCTCACTGACTATAAAGAATAGAGAAGGAAGGGCTTCAGTGACCGGCTGCCTGGTGACTTACAGCAGTCAGACTCTGACAGGATC

1  ATGGCTATGATGGAGGTCCAGGGGTCCAGCCTGGGACAGACCTGCCTGCTGTGATCTTCACAGTGCTCTTCCTGCAGTCTCTCTGT
  1  MetAlaMetMetGluValGlnGlySerLeuValGlyProSerLeuGlyGlnThrCysValLeuIleValIlePheThrValLeuLeuGlnSerLeuCys

181  GTGGCTGTAACTTACGTGTACTTTACCAACGAGCTCAGGACAGATGCAAGCTACTCCAAAAGTGGCATTGCTTGTTCTTAAAAGAA
 31  ValAlaValThrTyrValTyrPheThrAsnGluLeuLysGlnMetAsnGluLeuLysLysSerGlyIleAlaCysPheLeuLysGlu

271  GATGACAGTTATTGGGACCCCAATGACGAAGAGAGTATGAACAGCCCCTGCTGGCAAGTGCAACTCCGTCAGCTCGTTAGAAAG
 61  AspAspSerTyrTrpAspProAsnAspGluGluSerMetAsnSerProCysTrpGlnValLysTrpGlnLeuArgGlnLeuArgLys

361  ATGATTTTGAGAACCTCTGAGGAAGTTCTACAGTTCAAGAAACAACAAAATATTTCTCCCCTAGTGAGAGAAAGAGGTCCNCAG
 91  MetIleLeuArgThrSerGluGluValGlnPheLysAsnIleAsnIleSerProLeuValArgGluArgGlyProGln

451  AGAGTAGCAGCTCACATAACTGGGACCCAGAGGAAGAAGCAACACATTGTCTTCCAAACTCCAAGAATGAAAAGGCTCTGGGCCGCAAA
121  ArgValAlaAlaHisIleThrGlyThrGlnArgLysSerProAsnSerSerLysAsnGluLysAlaLeuGlyArgLys

541  ATAAACTCCTGGAATCATCAAGGAGGTGGGCCATTCATTCGAGCAACTGCACTTGGTCATCCATGAAAAAGG
151  IleAsnSerTrpAsnHisGlnGlyGlyGlyHisSerPheGluGlnLeuHisLeuValIleHisGluLysGly

631  TTTTACTACATCTATTCCCAAACATACTTTCGATTTCAGGAGGAAATAAAAGAAACACAAAGAACGACAAACAAATGGTCCAATATATT
181  PheTyrTyrIleTyrSerGlnThrTyrPheArgPheGlnGluGluIleLysGluThrLysAsnAspLysGlnMetValGlnTyrIle

721  TACAAATACACAAGTTATCCTGACCTATATTGTGATGAAAATGTGCTAGAAATAGTTGTTGATGAAAGATGCAGAATATGGACTCTAT
211  TyrLysTyrThrSerTyrProAspLeuTyrCysAspGluAsnValLeuLysLeuLysMetLysSerAlaArgAsnSerCysTrpSerLysAspAlaGluTyrGlyLeuTyr

811  TCCATCTATCAAGGGGAATATTTGAGCTTAAGGAGTTTTGTTTTCTGTAACAAATGACACTGACACTGATAGACATGGACCAT
241  SerIleTyrGlnGlyGluTyrLeuSerLeuLysGluAspAsnAspArgIlePheValSerValThrArgAsnGluHisLeuIleAspMetAspHis

901  GAAGCCAGTTTTTTCGGGGCCCTTTTAGTTGGCTAACTGACCTGGAAAGAAAAAGCAATAACCTCAAAGTGACTATTCAGTTTTCAGGAT
271  GluAlaSerPhePheGlyAlaPheLeuValGlyStp

991  GATACACTATGAAGATGTTTCAAAAAATCTGACCAAAACAAAACAGAAA
```

*FIG._1*

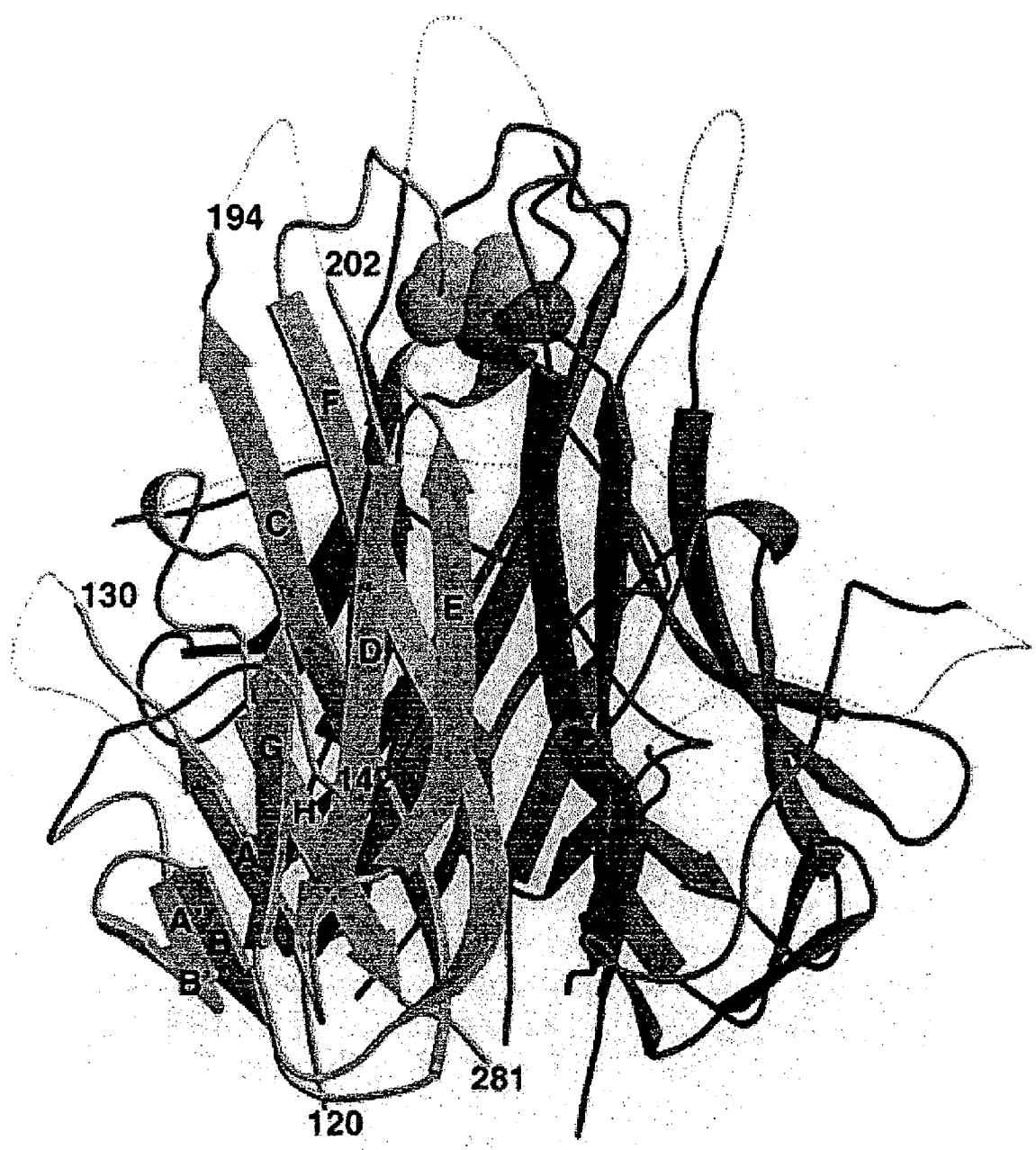
FIG._2A

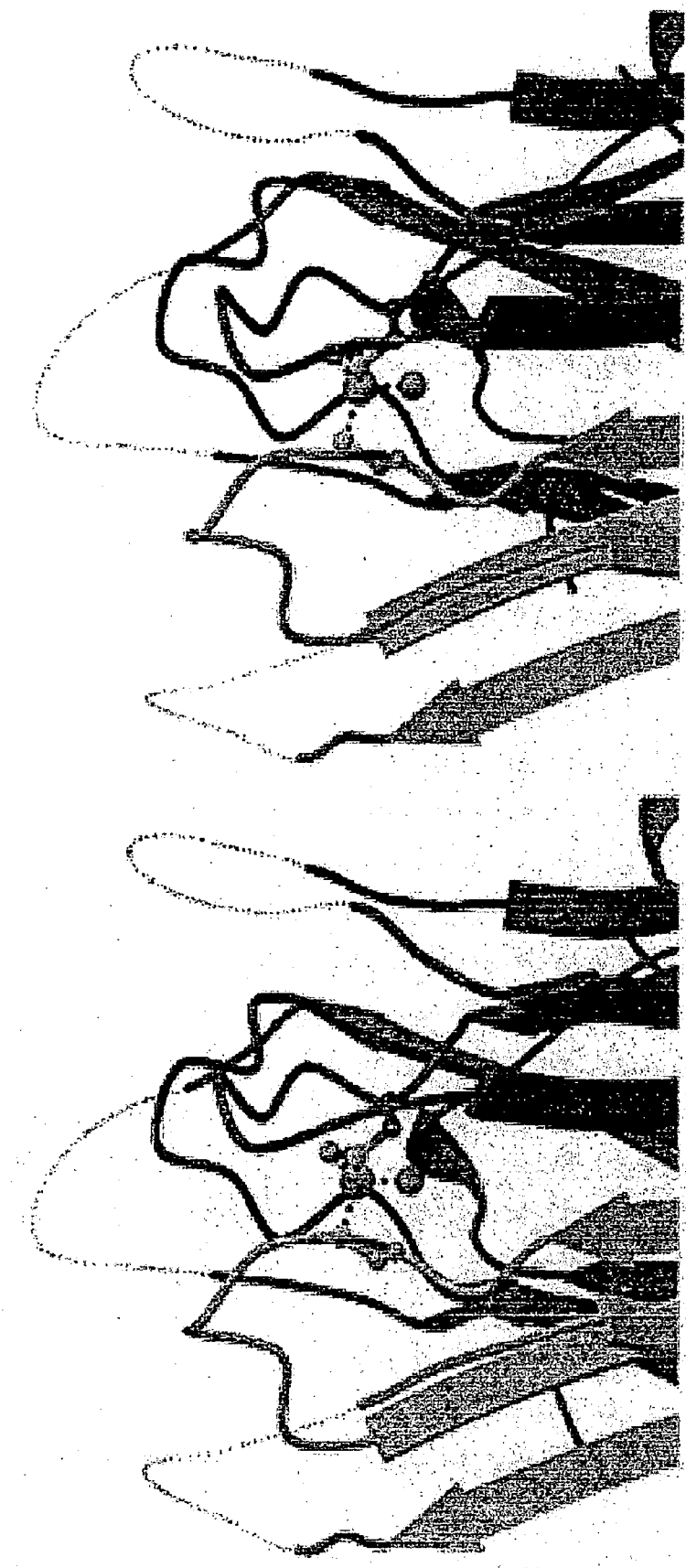
FIG._2B

Crystallographic Data

|  | Apo-2L (114-281) | Apo-2L (91-281) D218A | Apo-2L (91-281) D218A |
|---|---|---|---|
| Crystal |  |  |  |
| Space Group | $P6_3$ | R32 | R32 |
| Unit Cell (Å) | a=72.5 c=140 | a=66.4 c=197.6 | a=66.4 c=197.7 |
| Resolution (Å) | 3.9 | 1.9 | 1.3 |
| Coverage (%) | 94 (96) | 93 (99) | 100 (100) |
| $<I/\sigma(I)>$ | 5.9 | 10.1 | 12.4 |
| # Unique (hkl) | 3589 | 12680 | 41840 |
| Redundancy | 4.9 | 4.3 | 12.1 |
| $R_{symm}$ (%) | 15.4 (34) | 6.2 (27) | 6.4 (34) |
| # Protomers in ASU | 2 | 1 | 1 |
| Refinement |  |  |  |
| $R_{cryst}$ (%) | 33.8 | 20 |  |
| $R_{free}$ (%) | 27.6 | 22 |  |
| rmsd Bonds (Å) | 0.009 | 0.015 | 0.007 |
| rmsd Angles (°) | 1.79 | 2.0 | 1.41 |
| Average B-Values | — | 14 | 14 |
| # Water Molecules | 0 | 170 |  |

Rsymm $=\Sigma_h\Sigma_i(I_{hi}-<I_h>)/\Sigma_h I$ where $I_h$ is the mean structure factor intensity of i observations of symmetry-related reflections with Bragg index $h$. $R_{cryst}=\Sigma_h\Sigma_i||F_{obs}|-|F_{calc}||/\Sigma|F_{obs}|)$ where $F_{obs}$ and $F_{calc}$ are the observed and calculated structure factor amplitudes. $R_{free}=\Sigma_{(hkl)\varepsilon\tau}||Fobs_{(hkl)}|-k|F_{(hkl)}|/\Sigma_{(hkl)\varepsilon\tau}|Fobs_{(hkl)}|$ where the $\tau$ set of reflections is omitted from the refinement process. 10% of the data were included in the $\tau$ set for calculation of $R_{free}$ and not included in refinement. Values in parenthesis are for the highest resolution shell.

FIG._2C

```
                    A                                           A'    B'
                    →                                           →     →
           121       130       140       150       160            170
            •         •         •         •         •              •
Apo2L    RV AAHI TGTRGRSNTLSSPNSKNEKALGRKINSWESSRSGHSFLSNLHLR
TNF-β    KP AAHL IGD................PSKQNSLLWRANTDRAFLQDGFSLS
TNF-α    KP VAHV VAN................PQAEGQLQWLNRRANALLANGVELR
CD40L    QI AAHV ISE..............ASSKTTSVLQWAEKGYYTMSNNLVTLE
FasL     RK VAHL TGK...............SNSRSMPLEWEDTY.GIVLLSGVKYK
RANKL    QP FAHL TIN.........ATDIPSGSHKVSLSSWYHDR.GWAKISNMTFS

B                C                                D
              →                →                                →
                     180       190       200        210
                      •         •         •          •
Apo2L    NG.E LVI HEK GFYYIYSQT YFRFQEEIKENTKNDKQMVQYIYKYTS.YPD
TNF-β    NN.S LLV PTS GIYFVYSQV VFSGKAYSPKATSSPLYLAHEVQLFSSQYPF
TNF-α    DN.Q LVV PSE GLYLIYSQV LFKGQG....CPSTHVLLTHTISRIAVSYQT
CD40L    NGKQ LTV KRQ GLYYIYAQV TFCS.......NREASSQAPFIASLCLKSPG
FasL     KG.G LVI NET GLYFVYSKV YFRGQ......SCNNLPLSHKVYMRNSKYPQ
RANKL    NG.K LIV NQD GFYYLYANI CFRHHETSGDLATEYLQLMVYVTKTSIKIPS

E                     F              G
                 →                     →              →
         220       230         240           250        260
          •         •           •             •          •
Apo2L    PILLMKSARNSCWSKDAE.....YGLYSIYQ GGIFEL KENDRIFVSVTNE
TNF-β    HVPLLSSQKMVYPGLQE......PWLHSMYHGAAFQLTQGDQLSTHTDGI
TNF-α    KVNLLSAIKSPCQRETPEGAEAKPWYEPIYL GGVFQL EKGDRLSAEINRP
CD40L    RFERILLRAANTHSSAKP.....CGQQSIHL GGVFEL QPGASVFNVTDP
FasL     DLVMMEGKMMSYCTTGQ......MWARSSYL GAVFNL TSADHLYVNVSEL
RANKL    SHTLMKGGSTKYWSGNSE.....FHFYSINV GGFFKL RSGEEISIEVSNP

H
                   →
              270       280
               •         •
Apo2L    HLIDMDHE.AS FFGAF LVG
TNF-β    PHLVLSPS.TV FFGAF AL.
TNF-α    DYLLFAESGQV YFGII AL.
CD40L    SQVSHGTG.FT SFGLL KL.
FasL     SLVNFEES.QT FFGLY K..
RANKL    SLLDPDQD.AT YFGAF KVR
```

FIG._3

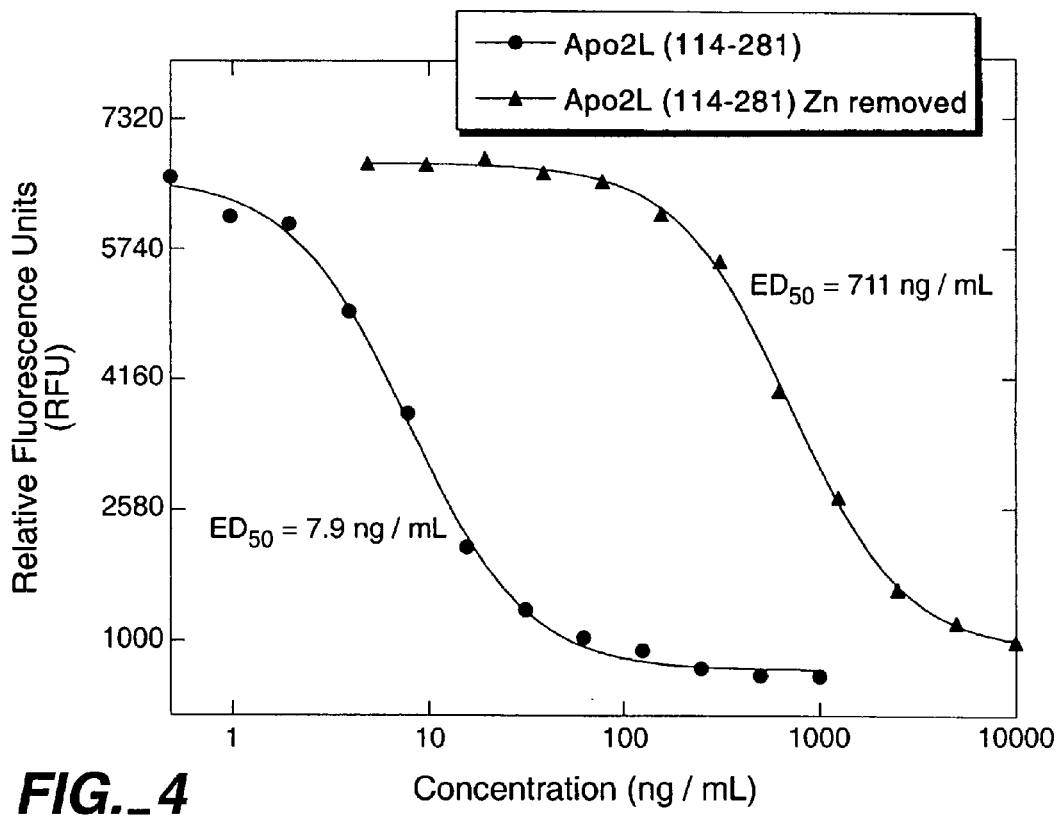
FIG._4
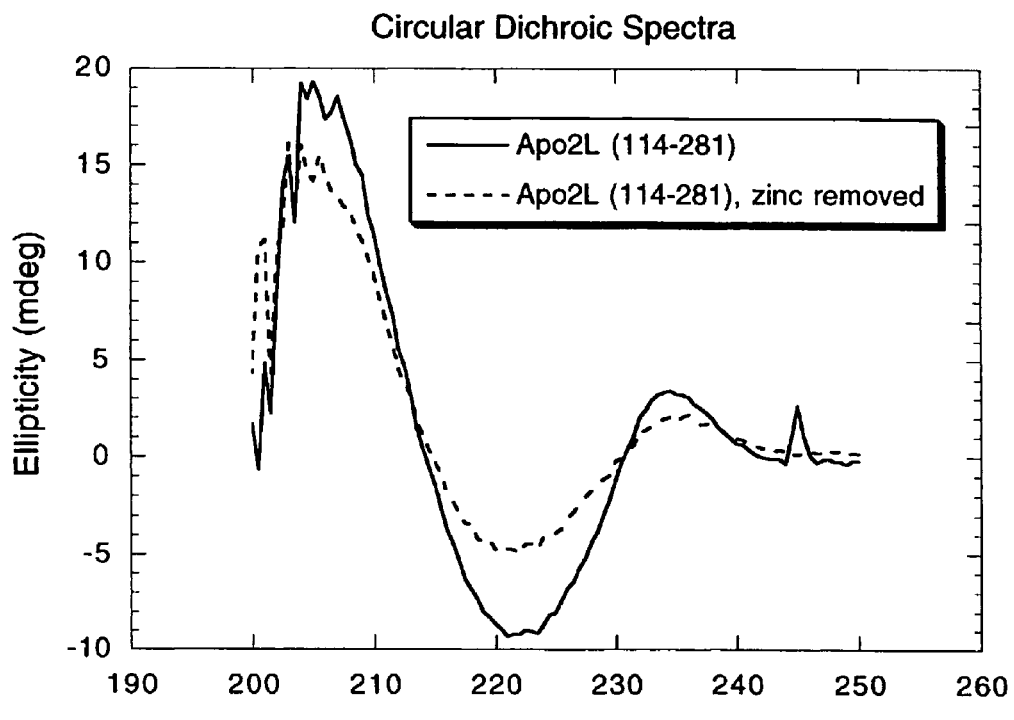
FIG._6

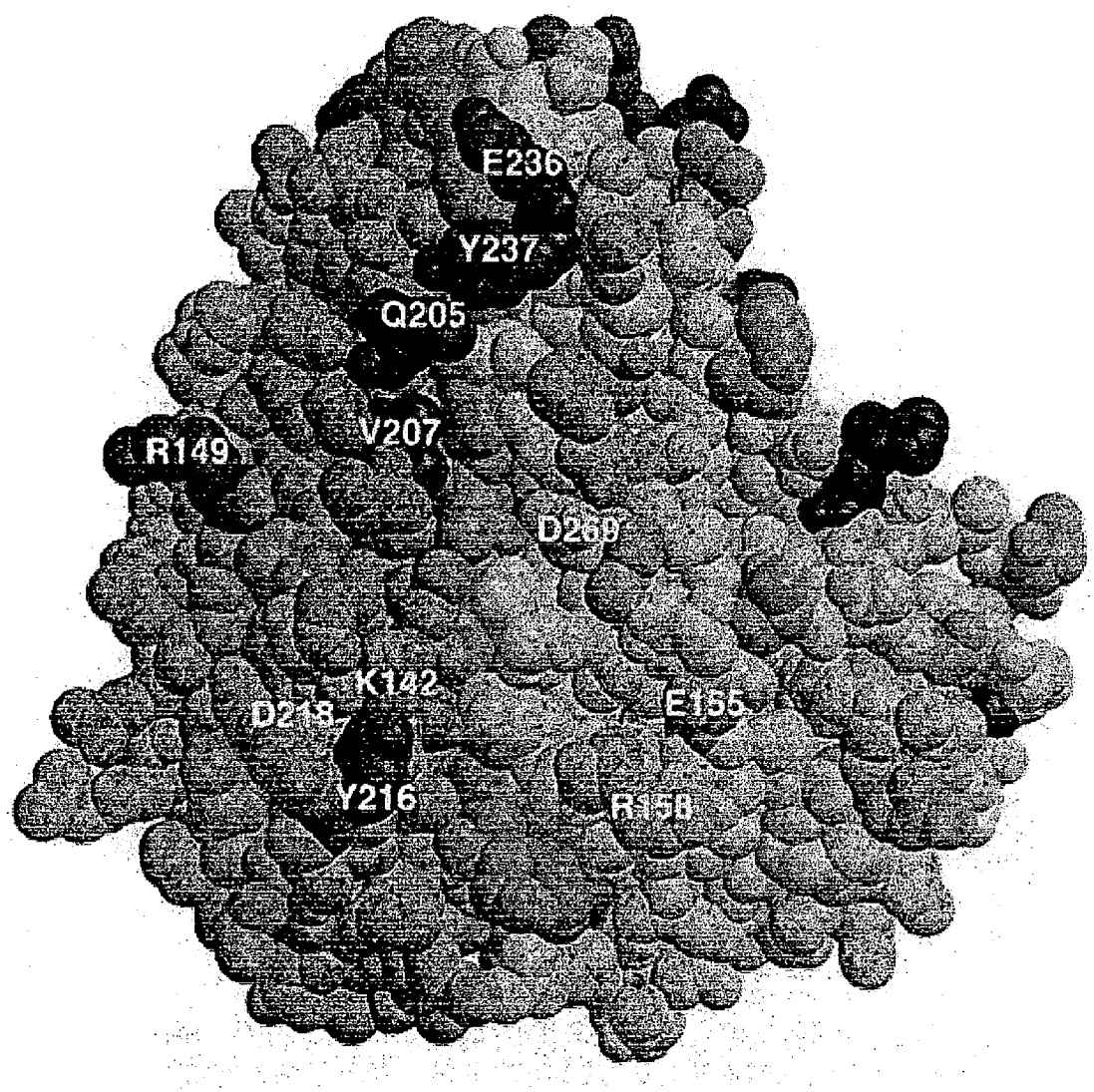
FIG._5

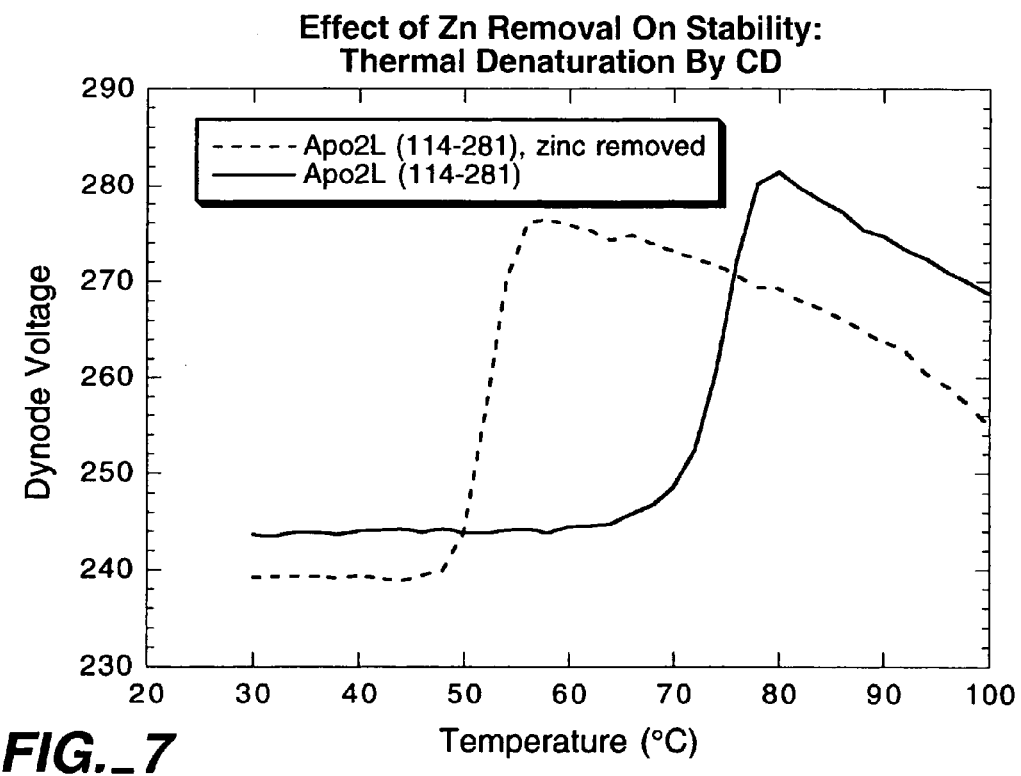
FIG._7
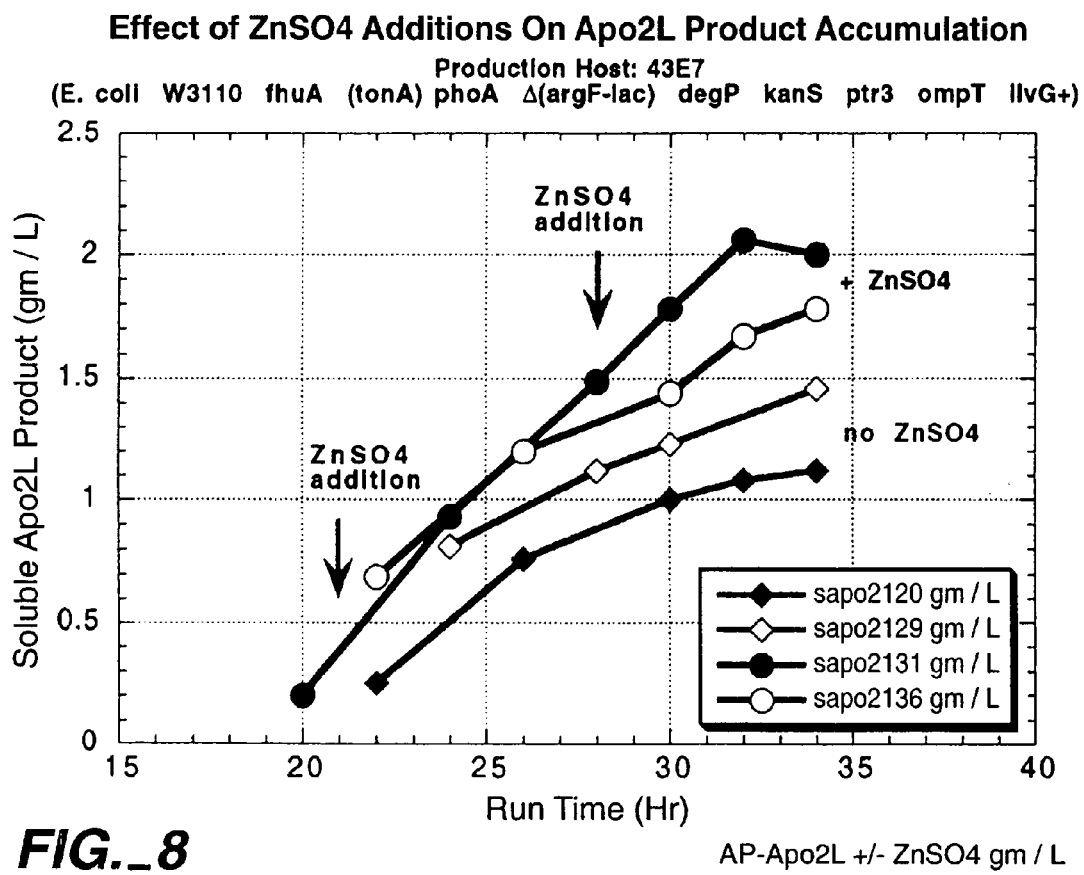
FIG._8

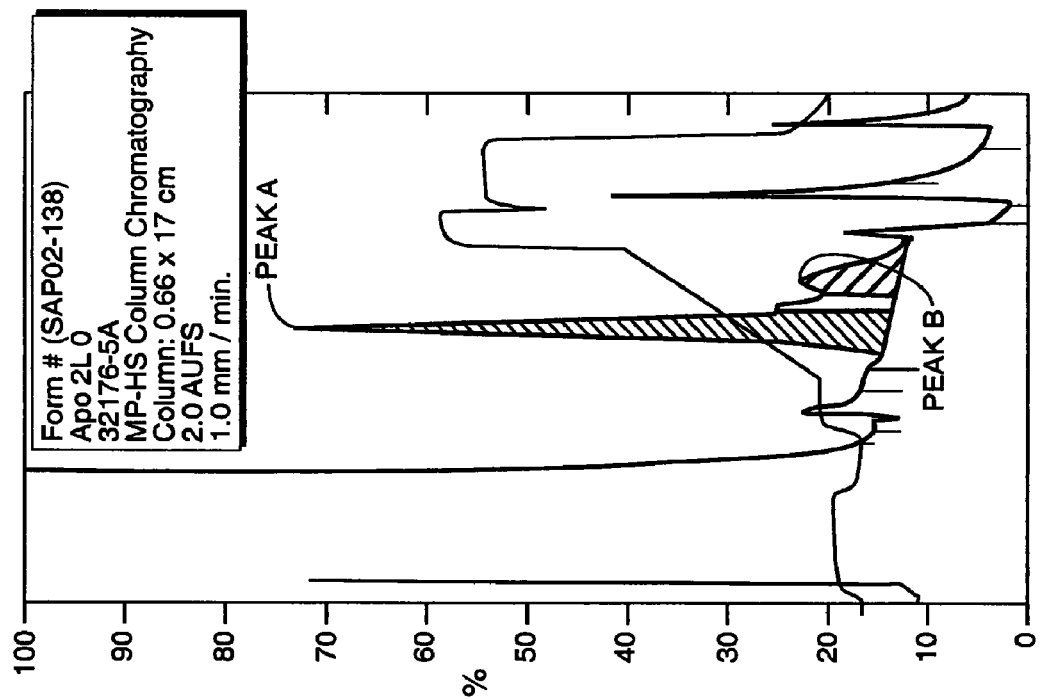
FIG._9B
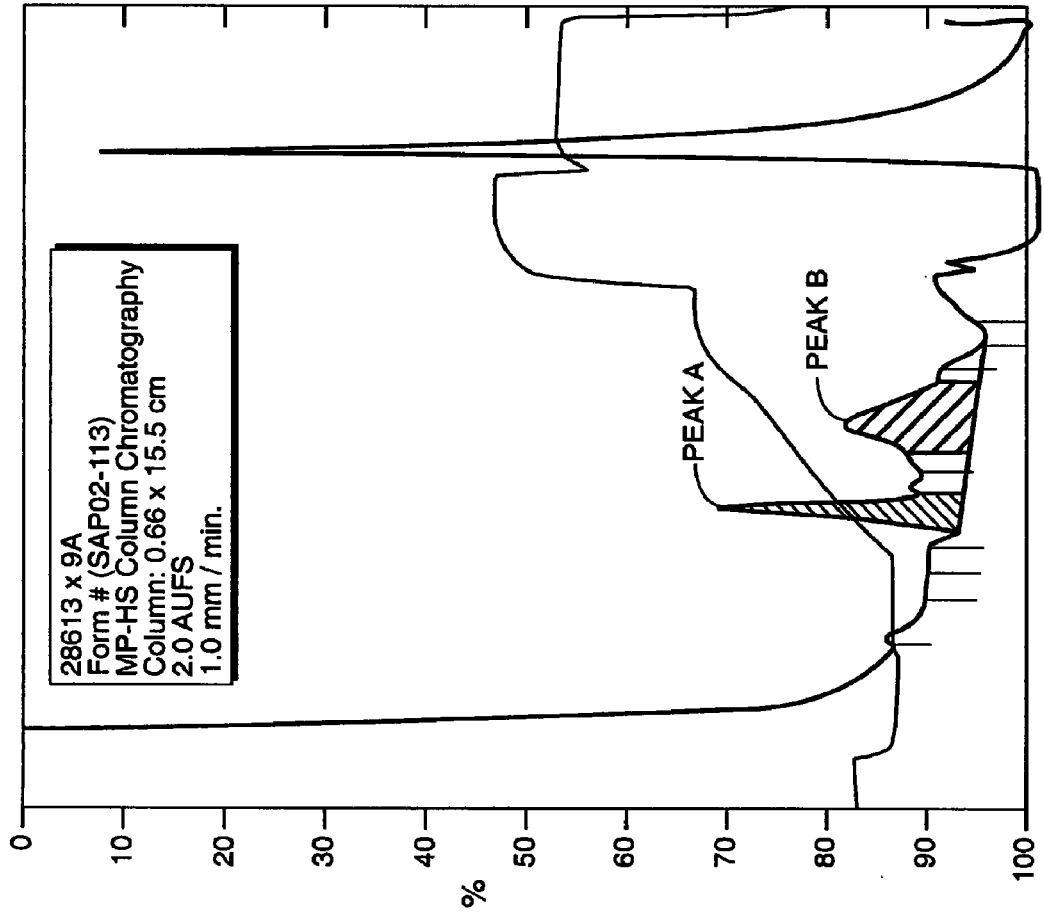
FIG._9A

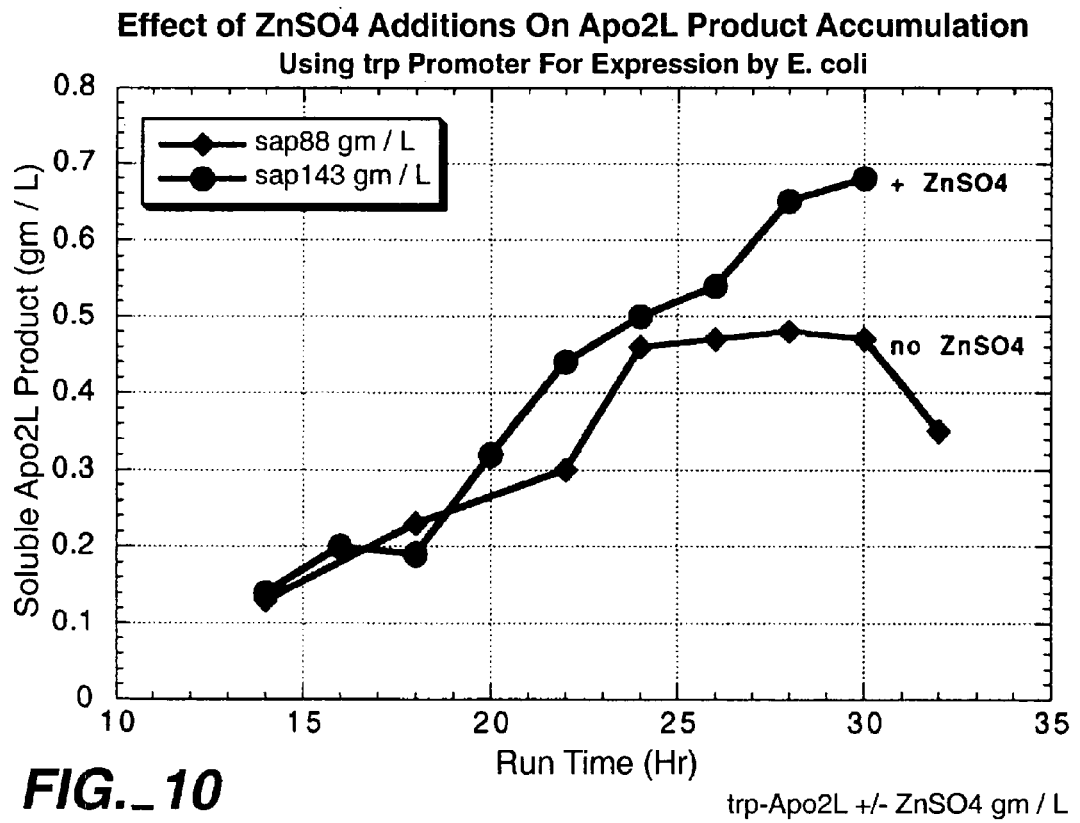
FIG._10
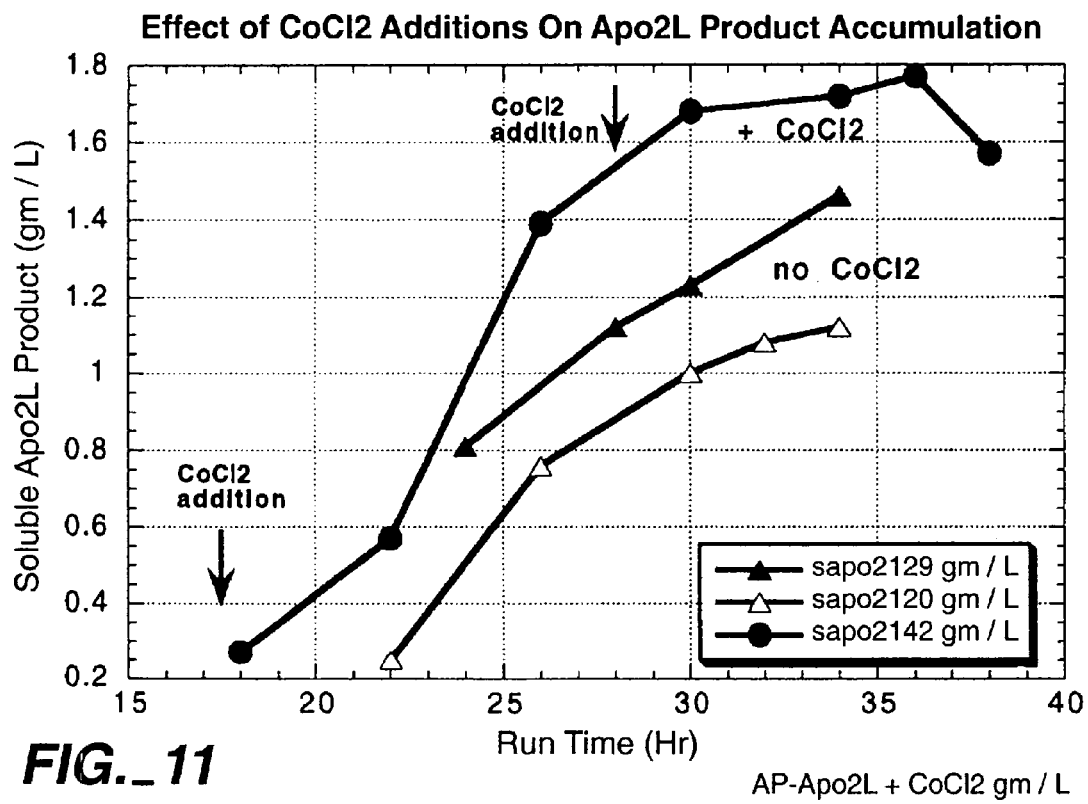
FIG._11

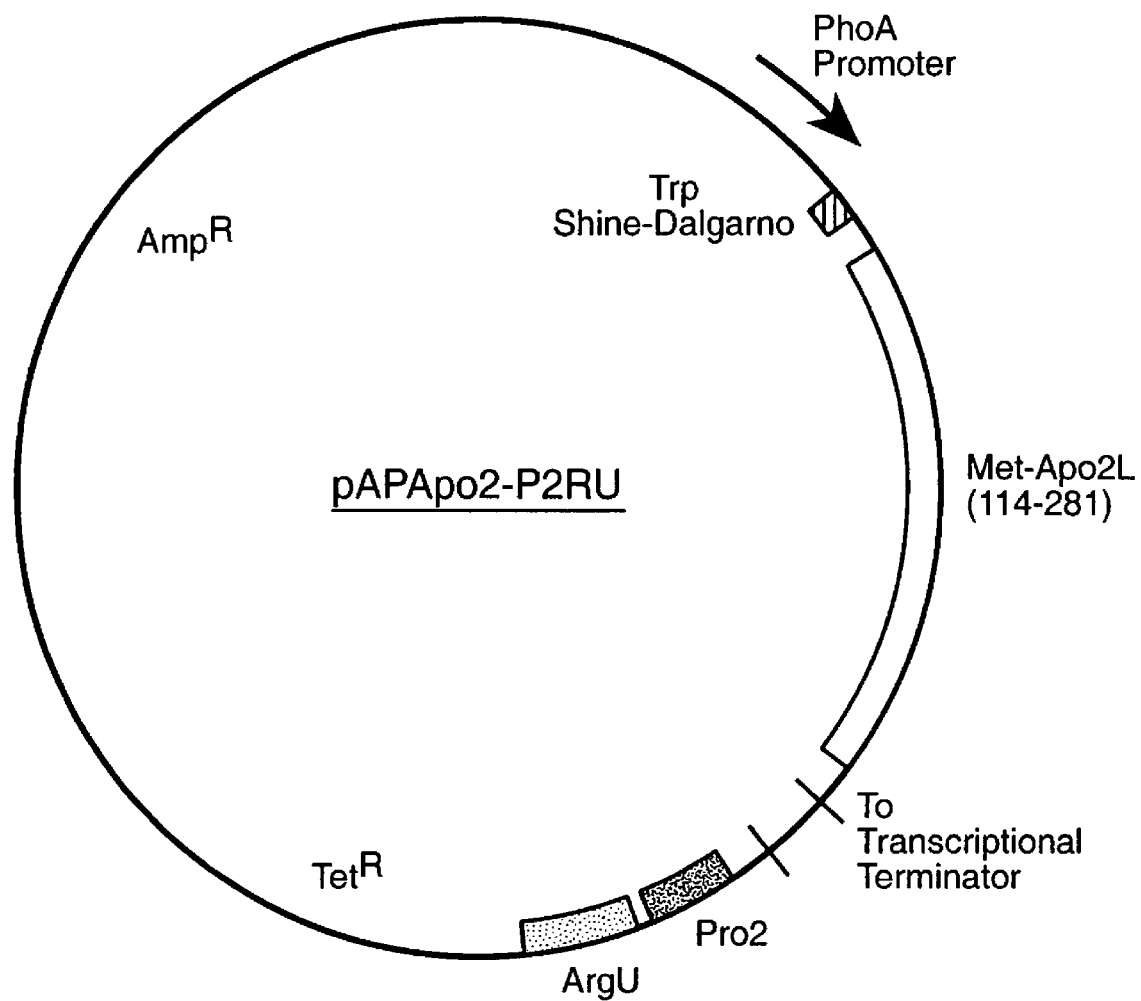
FIG._12

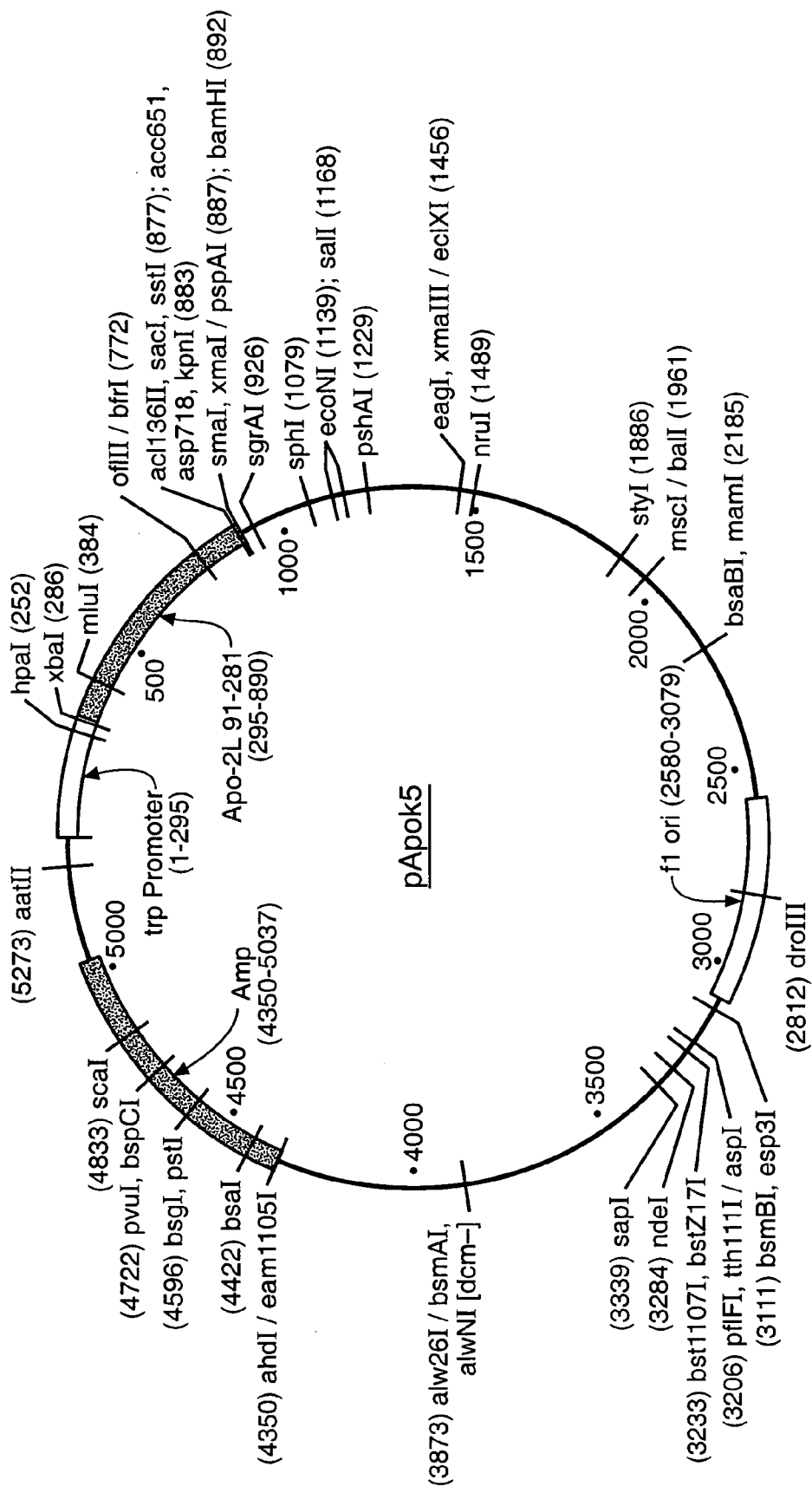
FIG._13

METHODS FOR MAKING APO-2 LIGAND USING DIVALENT METAL IONS

RELATED APPLICATIONS

This is a continuation application claiming priority to U.S. application Ser. No. 09/603,866 filed Jun. 26, 2000, now abandoned, which is a non-provisional application claiming priority under Section 119(e) to provisional application No. 60/141,342 filed Jun. 28, 1999, the contents of which are incorporated herein by reference.

FIELD OF THE INVENTION

The present invention relates generally to making Apo-2 ligand and Apo-2 ligand formulations using divalent metal ions, such as zinc or cobalt. The use of such Apo-2 ligand and Apo-2 ligand formulations having improved Apo-2L trimer formation and stability is also provided. The present invention also relates to Apo-2 ligand variants, particularly alanine substitution variants.

BACKGROUND OF THE INVENTION

Control of cell numbers in mammals is believed to be determined, in part, by a balance between cell proliferation and cell death. One form of cell death, sometimes referred to as necrotic cell death, is typically characterized as a pathologic form of cell death resulting from some trauma or cellular injury. In contrast, there is another, "physiologic" form of cell death which usually proceeds in an orderly or controlled manner. This orderly or controlled form of cell death is often referred to as "apoptosis" [see, e.g., Barr et al., *Bio/Technology*, 12:487-493 (1994); Steller et al., *Science*, 267:1445-1449 (1995)]. Apoptotic cell death naturally occurs in many physiological processes, including embryonic development and clonal selection in the immune system [Itoh et al., *Cell*, 66:233-243 (1991)].

Various molecules, such as tumor necrosis factor-α ("TNF-α"), tumor necrosis factor-β ("TNF-β" or "lymphotoxin-α"), lymphotoxin-β ("LT-β"), CD30 ligand, CD27 ligand, CD40 ligand, OX-40 ligand, 4-1BB ligand, Apo-1 ligand (also referred to as Fas ligand or CD95 ligand), Apo-2 ligand (also referred to as TRAIL, AIM-1 or AGP-1), and Apo-3 ligand (also referred to as TWEAK) have been identified as members of the tumor necrosis factor ("TNF") family of cytokines [See, e.g., Gruss and Dower, *Blood*, 85:3378-3404 (1995); Pitti et al., *J. Biol. Chem.*, 271:12687-12690 (1996); Wiley et al., *Immunity*, 3:673-682 (1995); Browning et al., *Cell*, 72:847-856 (1993); Armitage et al. *Nature*, 357:8.0-82 (1992), WO 97/01633 published Jan. 16, 1997; WO 97/25428 published Jul. 17, 1997; WO 97/46686 published Dec. 11, 1997; WO 97/33899 published Sep. 18, 1997; Marsters et al., *Curr. Biol.*, 8:525-528 (1998); Chicheportiche et al., *Biol. Chem.*, 272:32401-32410 (1997)]. Among these molecules, TNF-α, TNF-β, CD30 ligand, 4-1BB ligand, Apo-1 ligand, Apo-2 ligand (TRAIL) and Apo-3 ligand (TWEAK) have been reported to be involved in apoptotic cell death.

Induction of various cellular responses mediated by such TNF family cytokines is believed to be initiated by their binding to specific cell receptors. Two distinct TNF receptors of approximately 55-kDa (TNFR1) and 75-kDa (TNFR2) have been identified [Hohman et al., *J. Biol. Chem.*, 264: 14927-14934 (1989); Brockhaus et al., *Proc. Natl. Acad. Sci.*, 87:3127-3131 (1990); EP 417,563, published Mar. 20, 1991] and human and mouse cDNAs corresponding to both receptor types have been isolated and characterized [Loetscher et al., *Cell*, 61:351 (1990); Schall et al., *Cell*, 61:361 (1990); Smith et al., *Science*, 248:1019-1023 (1990); Lewis et al., *Proc. Natl. Acad. Sci.*, 88:2830-2834 (1991); Goodwin et al., *Mol. Cell. Biol.*, 11:3020-3026 (1991)]. Extensive polymorphisms have been associated with both TNF receptor genes [see, e.g., Takao et al., *Immunogenetics*, 37:199-203 (1993)]. Both TNFRs share the typical structure of cell surface receptors including extracellular, transmembrane and intracellular regions. The extracellular portions of both receptors are found naturally also as soluble TNF-binding proteins [Nophar, Y. et al., *EMBO J.*, 9:3269 (1990); and Kohno, T. et al., *Proc. Natl. Acad. Sci. U.S.A.*, 87:8331 (1990)]. The cloning of recombinant soluble TNF receptors was reported by Hale et al. [*J. Cell. Biochem. Supplement 15F*, 1991, p. 113 (P424)].

The extracellular portion of type 1 and type 2 TNFRs (TNFR1 and TNFR2) contains a repetitive amino acid sequence pattern of four cysteine-rich domains (CRDs) designated 1 through 4, starting from the $NH_2$-terminus. Each CRD is about 40 amino acids long and contains 4 to 6 cysteine residues at positions which are well conserved [Schall et al., supra; Loetscher et al., supra; Smith et al., supra; Nophar et al., supra; Kohno et al., supra]. In TNFR1, the approximate boundaries of the four CRDs are as follows: CRD1—amino acids 14 to about 53; CRD2—amino acids from about 54 to about 97; CRD3—amino acids from about 98 to about 138; CRD4—amino acids from about 139 to about 167. In TNFR2, CRD1 includes amino acids 17 to about 54; CRD2—amino acids from about 55 to about 97; CRD3—amino acids from about 98 to about 140; and CRD4—amino acids from about 141 to about 179 [Banner et al., *Cell*, 73:431-435 (1993)]. The potential role of the CRDs in ligand binding is also described by Banner et al., supra.

A similar repetitive pattern of CRDs exists in several other cell-surface proteins, including the p75 nerve growth factor receptor (NGFR) [Johnson et al., *Cell*, 47:545 (1986); Radeke et al., *Nature*, 325:593 (1987)], the B cell antigen CD40 [Stamenkovic et al., *EMBO J.*, 8:1403 (1989)], the T cell antigen OX40 [Mallet et al., *EMBO J.*, 9:1063 (1990)] and the Fas antigen [Yonehara et al., *J. Exp. Med.*, 169:1747-1756 (1989) and Itoh et al., *Cell*, 66:233-243 (1991)]. CRDs are also found in the soluble TNFR (sTNFR)-like T2 proteins of the Shope and myxoma poxviruses [Upton et al., *Virology*, 160:20-29 (1987); Smith et al., *Biochem. Biophys. Res. Commun.*, 176:335 (1991); Upton et al., *Virology*, 184:370 (1991)]. Optimal alignment of these sequences indicates that the positions of the cysteine residues are well conserved. These receptors are sometimes collectively referred to as members of the TNF/NGF receptor superfamily. Recent studies on p75NGFR showed that the deletion of CRD1 [Welcher, A. A. et al., *Proc. Natl. Acad. Sci. USA*, 88:159-163 (1991)] or a 5-amino acid insertion in this domain [Yan, H. and Chao, M. V., *J. Biol. Chem.*, 266:12099-12104 (1991)] had little or no effect on NGF binding [Yan, H. and Chao, M. V., supra]. p75 NGFR contains a proline-rich stretch of about 60 amino acids, between its CRD4 and transmembrane region, which is not involved in NGF binding [Peetre, C. et al., *Eur. J. Hematol.*, 41:414-419 (1988); Seckinger, P. et al., *J. Biol. Chem.*, 264:11966-11973 (1989); Yan, H. and Chao, M. V., supra]. A similar proline-rich region is found in TNFR2 but not in TNFR1.

The TNF family ligands identified to date, with the exception of lymphotoxin-α, are type II transmembrane proteins, whose C-terminus is extracellular. In contrast, most receptors in the TNF receptor (TNFR) family identified to date are type I transmembrane proteins. In both the TNF ligand and receptor families, however, homology identified between family members has been found mainly in the extracellular domain ("ECD"). Several of the TNF family cytokines, including TNF-α, Apo-1 ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines.

Recently, other members of the TNFR family have been identified. Such newly identified members of the TNFR family include CAR1, HVEM and osteoprotegerin (OPG) [Brojatsch et al., *Cell*, 87:845-855 (1996); Montgomery et al., *Cell*, 87:427-436 (1996); Marsters et al., *J. Biol. Chem.*, 272: 14029-14032 (1997); Simonet et al., *Cell*, 89:309-319 (1997)]. Unlike other known TNFR-like molecules, Simonet et al., supra, report that OPG contains no hydrophobic transmembrane-spanning sequence. OPG is believed to act as a decoy receptor, as discussed below.

Another new member of the TNF/NGF receptor family has been identified in mouse, a receptor referred to as GITR for "glucocorticoid-induced tumor necrosis factor receptor family-related gene" [Nocentini et al., *Proc. Natl. Acad. Sci. USA* 94:6216-6221 (1997)]. The mouse GITR receptor is a 228 amino acid type I transmembrane protein that is expressed in normal mouse T lymphocytes from thymus, spleen and lymph nodes. Expression of the mouse GITR receptor was induced in T lymphocytes upon activation with anti-CD3 antibodies, Con A or phorbol 12-myristate 13-acetate.

In Marsters et al., *Curr. Biol.*, 6:750 (1996), investigators describe a full length native sequence human polypeptide, called Apo-3, which exhibits similarity to the TNFR family in its extracellular cysteine-rich repeats and resembles TNFR1 and CD95 in that it contains a cytoplasmic death domain sequence [see also Marsters et al., *Curr. Biol.*, 6:1669 (1996)]. Apo-3 has also been referred to by other investigators as DR3, wsl-1, TRAMP, and LARD [Chinnaiyan et al., *Science*, 274: 990 (1996); Kitson et al., *Nature*, 384:372 (19961; Bodmer et al., *Immunity*, 6:79 (1997); Screaton et al., *Proc. Natl. Acad. Sci.*, 94:4615-4619 (1997)].

Pan et al. have disclosed another TNF receptor family member referred to as "DR4" [Pan et al., *Science*, 276:111-113 (1997)]. The DR4 was reported to contain a cytoplasmic death domain capable of engaging the cell suicide apparatus. Pan et al. disclose that DR4 is believed to be a receptor for the ligand known as Apo-2 ligand or TRAIL.

In Sheridan et al., *Science*, 277:818-821 (1997) and Pan et al., *Science*, 277:815-818 (1997), another molecule believed to be a receptor for the Apo-2 ligand (TRAIL) is described. That molecule is referred to as DR5 (it has also been alternatively referred to as Apo-2; TRAIL-R2, TRICK2 or KILLER [Screaton et al., *Curr. Biol.*, 7:693-696 (1997); Walczak et al., *EMBO J.*, 16:5386-5387 (1997); Wu et al., *Nature Genetics*, 17:141-143 (1997)]. Like DR4, DR5 is reported to contain a cytoplasmic death domain and be capable of signaling apoptosis.

Yet another death domain-containing receptor, DR6, was recently identified [Pan et al., *FEBS Letters*, 431:351-356 (1998)]. Aside from containing four putative extracellular domains and a cytoplasmic death, domain, DR6 is believed to contain a putative leucine-zipper sequence that overlaps with a proline-rich motif in the cytoplasmic region. The proline-rich motif resembles sequences that bind to src-homology-3 domains, which are found in many intracellular signal-transducing molecules.

A further group of recently identified TNFR family members are referred to as "decoy receptors," which are believed to function as inhibitors, rather than transducers of signaling. This group includes DCR1 (also referred to as TRID, LIT or TRAIL-R3) [Pan et al., *Science*, 276:111-113 (1997); Sheridan et al., *Science*, 277:818-821 (1997); McFarlane et al., *J. Biol. Chem.*, 272:25417-25420 (1997); Schneider et al., *FEBS Letters*, 416:329-334 (1997); Degli-Esposti et al., *J. Exp. Med.*, 186:1165-1170 (1997); and Mongkolsapaya et al., *J. Immunol.*, 160:3-6 (1998)] and DCR2 (also called TRUNDD or TRAIL-R4) [Marsters et al., *Curr. Biol.*, 7:1003-1006 (1997); Pan et al., *FEBS Letters*, 424:41-45 (1998); Degli-Esposti et al., *Immunity*, 7:813-820 (1997)], both cell surface molecules, as well as OPG [Simonet et al., supra] and DCR3 [Pitti et al., *Nature*, 396:699-703 (1998)], both of which are secreted, soluble proteins.

For a review of the TNF family of cytokines and their receptors, see Ashkenazi et al., *Science*, 281:1305-1308 (1998); Golstein, *Curr. Biol.*, 7:750-753 (1997); and Gruss and Dower, supra.

While zinc binding sites have been shown to play structural roles in protein-protein interactions in certain proteins involving diverse interfaces [Feese et al., *Proc. Natl. Acad. Sci.*, 91:3544-3548 (1994); Somers et al., *Nature*, 372:478-481 (1994); Raman et al., *Cell*, 95:939-950 (1998)], none of the previously structurally-characterized members of the TNF family (CD40 ligand, TNF-alpha, or TNF-beta) bind metals. The use of metal ions, such as zinc, in formulations of various hormones, such as human growth hormone (hGH), has been described in the literature. [See, e.g., WO 92/17200 published Oct. 15, 1992). Zinc involvement in hGH binding to receptors was likewise described in WO 92/03478 Published Mar. 5, 1992. The roles of zinc binding in interferon-alpha dimers and interferon-beta dimers were reported in Walter et al., *Structure*, 4:1453-1463 (1996) and Karpusas et al., *Proc. Natl. Acad. Sci.*, 94:11813-11818 (1997), respectively.

The structures and biological roles of various metal ions such as zinc have been reviewed in the art, see, e.g., Christianson et al., *Advances in Protein Chemistry*, 42:281-355 (1991).

SUMMARY OF THE INVENTION

The present invention is based on the discovery that the inclusion of one or more divalent metal ions in methods or processes for making Apo-2 ligand, or formulations containing Apo-2 ligand, results in increased yield and stability of Apo-2 ligand trimers. It is presently believed that such inclusion of one or more divalent metal ions may also improve folding of Apo-2 ligand or Apo-2L trimer assembly upon expression in recombinant cell culture. In oxidative environments, free cysteines on Apo-2L monomers may form intermolecular disulfide bridges, giving rise to free-standing Apo-2L dimers as well as disulfide-linked Apo-2L dimer species within trimeric forms of Apo-2L. Such formation of Apo-2L dimers may lead to aggregation, precipitation, and/or inactivation of Apo-2L. The presence of divalent metal ions in the methods and formulations described herein may protect against such disulfide bond formation. It appears that inclusion of divalent metal ions during the process of synthesis and assembly of Apo-2L trimers may further improve accumulation and recovery of properly folded, homotrimeric Apo-2L. Applicants have found that Apo-2 ligand trimers are approximately 10-fold more active (in cytotoxic activity in mammalian cancer cells) as compared to disulfide-linked Apo-2L dimers.

While the description of the invention herein is primarily directed to Apo-2 ligand, the use of divalent metal ions to make or stabilize trimers of various other proteins is contemplated. Such other proteins particularly include those proteins which require trimer formation for biological activity, for instance, various members of the TNF family.

In one embodiment, the invention provides a method of making Apo-2 ligand using one or more divalent ions. The methods include the steps of providing a host cell comprising a replicable vector containing a nucleic acid encoding Apo-2 ligand, providing culture media containing one or more divalent metal ions, culturing the host cell in the culture media under conditions sufficient to express the Apo-2 ligand, and recovering the Apo-2 ligand from the host cells or the cell culture media. Optionally, one or more divalent metal ions are used during the recovery or purification process.

In another embodiment, the invention provides a formulation comprising Apo-2 ligand and one or more divalent metal ions. The composition may be a pharmaceutically acceptable formulation useful, for instance, in inducing or stimulating apoptosis in mammalian cancer cells.

A further embodiment of the invention provides articles of manufacture and kits that include such Apo-2 ligand formulations containing one or more divalent metal ions. The articles of manufacture and kits include a container, a label on the container, and a formulation contained within the container. The label on the container indicates that the formulation can be used for certain therapeutic or non-therapeutic applications. The formulation contains Apo-2 ligand and one or more divalent ions.

In another embodiment, the invention provides Apo-2 ligand polypeptides made in accordance with the methods described herein. Such Apo-2 ligands may comprise amino acids 114-281 of FIG. 1 (SEQ ID NO:1), amino acids 1-281 of FIG. 1 (SEQ ID NO:1), as well as biologically active fragments or variants thereof.

In a still further embodiment, the invention provides Apo-2 ligand variants. Particularly, the invention provides Apo-2 ligand variants comprising one or more amino acid substitutions in the native sequence of Apo-2 ligand (FIG. 1; SEQ ID NO:1). Apo-2 ligand variants comprising alanine substitutions are provided in Table I below. The invention also provides nucleic acid molecules encoding such Apo-2L variants and vectors and host cells containing nucleic acid molecules encoding the Apo-2L variants.

BRIEF DESCRIPTION OF THE DRAWINGS

FIG. 1 shows the nucleotide sequence of human Apo-2 ligand cDNA (SEQ ID NO:2) and its derived amino acid sequence (SEQ ID NO:1). The "N" at nucleotide position 447 (in SEQ ID NO:2) is used to indicate the nucleotide base may be a "T" or "G".

FIG. 2 provides the crystal structure of Apo-2L. FIG. 2A shows a view of the trimer along the three fold axis. Each monomer is identical. The ordered protein structure commences at residue 120, residues 131-141 are disordered, as are residues 195-201 (marked as dashed lines). The zinc binding site including the three symmetry related cysteines and the solvent ligand are shown as space filling diagrams. FIG. 2B provides cross-eyed stereo close up view of the zinc binding site; the angles between Sγ-zinc-Sγ are 112° and the Sγ-zinc-solvent angles are 107° with 2.3 Angstrom zinc-sulfur and 2.3 Angstrom zinc-solvent bond distances. FIGS. 2 (and 5) were made with the programs Molscript [Kraulis et al., *J. Appl. Cryst.*, 24:946-950 (1991)] and Raster3D [Merrit et al., *Acta Cryst.*, D50:869-873 (1994)]. FIG. 2C provides a summary of the crystallographic data from the experiment described in Example 2.

FIG. 3 shows a sequence alignment of selected TNF family members: Apo2L (SEQ ID NO:1); TNF-beta (SEQ ID NO:3); TNF-alpha (SEQ ID NO:4); CD40L (SEQ ID NO:5); FasL (SEQ ID NO:6); RANKL (SEQ ID NO:7). Arrows over the sequence indicate beta-strands in Apo2L. The numbering over the aligned sequences corresponds to the Apo2L sequence numbering provided in FIG. 1 (SEQ ID NO:1).

FIG. 4 provides bioassay data showing the functional importance of the zinc binding site. SK-MES-1 cell viability was determined by a fluorescence assay of metabolic activity after overnight incubation with various concentrations of Apo-2L (form 114-281), or Apo-2L (form 114-281) treated with chelating agents to remove the zinc.

FIG. 5 shows mutational analysis mapped onto a space-filling model of Apo-2L. The trimer is oriented as in FIG. 2. Residues with a greater than 5-fold decrease in bioactivity when mutated to alanine are labeled and darkly shaded. Other residues that have been mutated are shown in medium shading and a few of these residues are also labeled.

FIG. 6 shows circular dichroic spectra of Apo-2L (form 114-281) before and after treatment to remove the bound zinc.

FIG. 7 shows thermal denaturation of Apo-2L before and after zinc removal monitored by circular dichroism at 225 nm. The dynode voltage is reported for 2 micromolar solutions of Apo-2L.

FIG. 8 shows the effect (time course) of $ZnSO_4$ additions on soluble Apo-2L product accumulation (gm/L) in an *E. coli* expression system using an AP promoter.

FIG. 9 shows the elution profiles from MPHS chromatography of cell lysates from the *E. coli* expression system (see Example 8) conducted in the presence or absence of $ZnSO_4$.

FIG. 10 shows the effect (time course) of $ZnSO_4$ addition on soluble Apo-2L product accumulation (gm/L) in an *E. coli* expression system using a trp promoter.

FIG. 11 shows the effect (time course) of $CoCl_2$ addition on soluble Apo-2L product accumulation (gm/L) in an *E. coli* expression system using an AP promoter.

FIG. 12 shows the pAPApo2-P2RU plasmid construct.

FIG. 13 shows the pAPOK5 plasmid construct.

DETAILED DESCRIPTION OF THE PREFERRED EMBODIMENTS

I. Definitions

The terms "Apo-2 ligand", "Apo-2L", and "TRAIL" are used herein to refer to a polypeptide sequence which includes amino acid residues 114-281, inclusive, 95-281, inclusive, residues 92-281, inclusive, residues 91-281, inclusive, residues 41-281, inclusive, residues 15-281, inclusive, or residues 1-281, inclusive, of the amino acid sequence shown in FIG. 1 (SEQ ID NO:1), as well as biologically active fragments, deletional, insertional, or substitutional variants of the above sequences. In one embodiment, the polypeptide sequence comprises residues 114-281 of FIG. 1 (SEQ ID NO:1). Optionally, the polypeptide sequence comprises residues 92-281 or residues 91-281 of FIG. 1 (SEQ ID NO:1). The Apo-2L polypeptides may be encoded by the native nucleotide sequence shown in FIG. 1 (SEQ ID NO:2). Optionally, the codon which encodes residue Pro119 (FIG. 1; SEQ ID NO:2) may be "CCT" or "CCG". In another preferred embodiment, the fragments or variants are biologically active and have at least about 80% amino acid sequence identity, more preferably at least about 90% sequence identity, and even more preferably, at least 95%, 96%, 97%, 98%, or 99% sequence identity with any one of the above sequences. The definition encompasses substitutional variants of Apo-2 ligand in which at least one of its native amino acids are substituted by an alanine residue. Preferred substitutional variants include one or more of the residue substitutions identified in Table I below. The definition also encompasses a native sequence Apo-2 ligand isolated from an Apo-2 ligand source or prepared by recombinant or synthetic methods. The Apo-2 ligand of the invention includes the polypeptides referred to as Apo-2 ligand or TRAIL disclosed in WO97/01633 published Jan. 16, 1997 and WO97/25428 published Jul. 17, 1997. The terms "Apo-2 ligand" or "Apo-2L" are used to refer generally to forms of the Apo-2 ligand which include monomer, dimer or trimer forms of the polypeptide. All numbering of amino acid residues referred to in the Apo-2L sequence use the numbering according to FIG. 1 (SEQ ID NO:1), unless specifically stated otherwise. For instance, "D203" or "Asp203" refers to the aspartic acid residue at position 203 in the sequence provided in FIG. 1 (SEQ ID NO:1).

The term "Apo-2 ligand extracellular domain" or "Apo-2 ligand ECD" refers to a form of Apo-2 ligand which is essentially free of transmembrane and cytoplasmic domains. Ordinarily, the ECD will have less than 1% of such transmembrane and cytoplasmic domains, and preferably, will have less than 0.5% of such domains.

The term "Apo-2 ligand monomer" or "Apo-2L monomer" refers to a covalent chain of an extracellular domain sequence of Apo-2L.

The term "Apo-2 ligand dimer" or "Apo-2L dimer" refers to two Apo-2L monomers joined in a covalent linkage via a disulfide bond. The term as used herein includes free standing Apo-2L dimers and Apo-2L dimers that are within trimeric forms of Apo-2L (i.e., associated with another Apo-2L monomer).

The term "Apo-2 ligand trimer" or "Apo-2L trimer" refers to three Apo-2L monomers that are non-covalently associated.

"TNF family member" is used in a broad sense to refer to various polypeptides that share some similarity to tumor necrosis factor (TNF) with respect to structure or function. Certain structural and functional characteristics associated with the TNF family of polypeptides are known in the art and described, for example, in the above Background of the Invention. Such polypeptides include but are not limited to those polypeptides referred to in the art as TNF-alpha, TNF-beta, CD40 ligand, CD30 ligand, CD27 ligand, OX-40 ligand, 4-1BB ligand, Apo-1 ligand (also referred to as Fas ligand or CD95 ligand), Apo-2 ligand (also referred to as TRAIL), Apo-3 ligand (also referred to as TWEAK), APRIL, OPG ligand (also referred to as RANK ligand, ODF, or TRANCE), and TALL-1 (also referred to as BlyS, BAFF or THANK) [See, e.g., Gruss and Dower, Blood, 85:3378-3404 (1995); Pitti et al., J. Biol. Chem., 271:12687-12690 (1996); Wiley et al., Immunity, 3:673-682 (1995); Browning et al., Cell, 72:847-856 (1993); Armitage et al. Nature, 357:80-82 (1992), WO 97/01633 published Jan. 16, 1997; WO 97/25428 published Jul. 17, 1997; Marsters et al., Curr. Biol., 8:525-528 (1998); Chicheportiche et al., Biol. Chem., 272:32401-32410 (1997); Hahne et al., J. Exp. Med., 188:1185-1190 (1998); WO98/28426 published Jul. 2, 1998; WO98/46751 published Oct. 22, 1998; WO/98/18921 published May 7, 1998; Moore et al., Science, 285:260-263 (1999); Shu et al., J. Leukocyte Biol., 65:680 (1999); Schneider et al., J. Exp. Med., 189: 1747-1756 (1999); Mukhopadhyay et al., J. Biol. Chem., 274:15978-15981 (1999)].

The term "epitope tagged" when used herein refers to a chimeric polypeptide comprising Apo-2 ligand, or a portion thereof, fused to a "tag polypeptide". The tag polypeptide has enough residues to provide an epitope against which an antibody can be made, yet is short enough such that it does not interfere with activity of the Apo-2 ligand. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

The term "divalent metal ion" refers to a metal ion having two positive charges. Examples of divalent metal ions for use in the present invention include but are not limited to zinc, cobalt, nickel, cadmium, magnesium, and manganese. Particular forms of such metals that may be employed include salt forms (e.g., pharmaceutically acceptable salt forms), such as chloride, acetate, carbonate, citrate and sulfate forms of the above mentioned divalent metal ions. A preferred divalent metal ion for use in the present invention is zinc, and more preferably, the salt form, zinc sulfate. Divalent metal ions, as described herein, are preferably employed in concentrations or amounts (e.g., effective amounts) which are sufficient to, for example, (1) enhance storage stability of Apo-2L trimers over a desired period of time, (2) enhance production or yield of Apo-2L trimers in a recombinant cell culture or purification method, (3) enhance solubility (or reduce aggregation) of Apo-2L trimers, or (4) enhance Apo-2L trimer formation.

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the Apo-2 ligand natural environment will not be present. Ordinarily, however, isolated protein will be prepared by at least one purification step.

An "isolated" Apo-2 ligand nucleic acid molecule is a nucleic acid molecule that is identified and separated from at least one contaminant nucleic acid molecule with which it is ordinarily associated in the natural source of the Apo-2 ligand nucleic acid. An isolated Apo-2 ligand nucleic acid molecule is other than in the form or setting in which it is found in nature. Isolated Apo-2 ligand nucleic acid molecules therefore are distinguished from the Apo-2 ligand nucleic acid molecule as it exists in natural cells. However, an isolated Apo-2 ligand nucleic acid molecule includes Apo-2 ligand nucleic acid molecules contained in cells that ordinarily express Apo-2 ligand where, for example, the nucleic acid molecule is in a chromosomal location different from that of natural cells.

"Percent (%) amino acid sequence identity" with respect to the sequences identified herein is defined as the percentage of amino acid residues in a candidate sequence that are identical with the amino acid residues in the Apo-2 ligand sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art can determine appropriate parameters for measuring alignment, including assigning algorithms needed to achieve maximal alignment over the full-length sequences being compared. For purposes herein, percent amino acid identity values can be obtained using the sequence comparison computer program, ALIGN-2, which was authored by Genentech, Inc. and the source code of which has been filed with user documentation in the US Copyright Office, Washington, D.C., 20559, registered under the US Copyright Registration No. TXU510087. The ALIGN-2 program is publicly available through Genentech, Inc., South San Francisco, Calif. All sequence comparison parameters are set by the ALIGN-2 program and do not vary.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Biologically active" or "biological activity" for the purposes herein means (a) having the ability to induce or stimulate apoptosis in at least one type of mammalian cancer cell or virally-infected cell in vivo or ex vivo; (b) capable of raising an antibody, i.e., immunogenic; (c) capable of binding and/or stimulating a receptor for Apo-2L; or (d) retaining the activity of a native or naturally-occurring Apo-2L polypeptide.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis or DNA electrophoresis.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer.

The terms "treating", "treatment" and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

II. Compositions and Methods of the Invention

A novel cytokine related to the TNF ligand family, the cytokine identified herein as "Apo-2 ligand" has been described. The predicted mature amino acid sequence of human Apo-2 ligand contains 281 amino acids, and has a calculated molecular weight of approximately 32.5 kDa. The absence of a signal sequence and the presence of an internal hydrophobic region suggests that Apo-2 ligand is a type II transmembrane protein. Soluble extracellular domain Apo-2 ligand polypeptides have also been described. See, e.g., WO97/25428 published Jul. 17, 1997. Apo-2L substitutional variants have further been described. Alanine scanning techniques have been utilized to identify various substitutional variant molecules having biological activity.

Particular substitutional variants of the Apo-2 ligand include those in which at least one amino acid is substituted by an alanine residue. These substitutional variants are identified, for example, as "D203A"; "D218A" and "D269A." This nomenclature is used to identify Apo-2 ligand variants wherein the aspartic acid residues at positions 203, 218, and/or 269 (using the numbering shown in FIG. 1 SEQ ID NO:1)) are substituted by alanine residues. Optionally, the Apo-2L variants may comprise one or more of the alanine substitutions which are recited in Table I below.

The x-ray crystal structure of the extracellular domain of Apo-2 ligand is now provided in the present invention, and alanine-scanning mutagenesis has been performed to provide the mapping of its receptor contact regions. The structure obtained for Apo-2 ligand reveals a homotrimeric protein which contains a novel divalent metal ion (zinc) binding site that coordinates the interaction of the Apo-2 ligand trimer molecule's three subunits.

The x-ray structure of Apo-2L was determined by molecular replacement using a model of TNF-alpha [Eck et al., $J.$ $Biol.$ $Chem.,$ 264:17595-17605 (1989)] and refined to 3.9 Angstrom (for the 114-281 residue form) and 1.3 Angstrom (for the D218A variant; 91-281 form). Like other members of the TNF family, Apo-2L appears to comprise a compact trimer formed of three jelly roll monomers which bury approximately 5100 Angstrom$^2$ (1700 Angstrom$^2$ per monomer) to form the globular trimer (See FIG. 2A). The position of the core beta-strands was well conserved compared to the other structurally characterized members of the TNF family, TNF-alpha [Eck et al., supra; Jones et al., $Nature,$ 338:225-228 (1989)], TNF-beta [Eck et al., $J.$ $Biol.$ $Chem.,$ 267:2119-2122 (1992)], and CD40L [Karpusas et al., $Structure,$ 3:1031-1039 (1995)], with a r.m.s.d. of 0.8 Angstrom when compared to the core strands of TNF-alpha or TNF-beta. None of the residues in the Apo-2L trimer interface appear to be absolutely conserved across the sequences of the all the presently known human TNF family members; however, the hydrophobic chemical nature of these residues is preserved. (See FIG. 3). The conserved residues in the Apo-2L trimer interface cluster near the base (the widest part of the trimer) and along the three-fold axis. Near the top of the Apo-2L trimer interface in the vicinity of Cys230, the structures appear to diverge, and the conformation of the 190's and 230's loops are variable in each structure.

In contrast to the beta-scaffold core, the structure of the loops and receptor binding surfaces varies considerably among the TNF family members. One difference between the structure of Apo-2 ligand and the structures of TNF-alpha, TNF-beta, and CD40L is the connections between strands A and A'. In TNF-alpha, TNF-beta, and CD40L, strand A is followed by a compact loop. In Apo-2 ligand, a 15-residue insertion lengthens this loop and alters its conformation. The first part of the loop (residues 131 to 141) is disordered while the second part of the loop (residues 142 to 154) crosses the surface of the molecule from one monomer-monomer interface to the next (see FIG. 2A) with a conformation that resembles CD40L in its C-terminal portion.

Applicants surprisingly found a novel divalent metal ion (zinc) binding site buried near the top of the trimerization interface. The TNF family members can be divided by sequence analysis into three groups with respect to Cys230: (1) proteins such as TNF-alpha and Fas ligand in which a cysteine residue at the position corresponding to Cys230 is accompanied by another cysteine in the adjacent loop (the 194-203 loop in Apo-2L) with which it can form a disulfide bridge precluding it from interacting with a metal ion, (2) proteins without a cysteine corresponding to Cys230 (such as TNF-beta and OPGL), and (3) proteins which have only one cysteine residue corresponding to Cys230. Apo-2L and its orthologs in other species meet the latter criteria (i.e., proteins which have only Cys230) and are expected to bind divalent metal ions at the trimer surface. The conformation of the main chain immediately prior to Cys230 in Apo-2L differs from the disulfide containing TNF family members such as TNF-alpha and CD40L. In Apo-2L, the side chain of Cys230 is oriented towards the interface instead of away from it.

The Cys230 residue in each Apo-2L monomer point inward toward the trimer axis and coordinate a divalent metal ion in conjunction with an interior solvent molecule. This divalent metal ion binding site exhibits slightly distorted tetrahedral geometry with bonds and angles appropriate for a zinc binding site and is completely inaccessible to solvent (see FIG. 2B). The identity of the bound metal was confirmed using inductively coupled plasma atomic emission spectrometry (ICP-AES) (see Example 5). In a quantitative analysis for Cd, Co, Zn, Ni, and Cu using ICP-AES, 0.79 moles of Zn and 0.06 moles of Co per molecule of Apo-2L trimer were detected demonstrating that the bound ion in the structure was zinc at approximately a one to one molar ratio (see Example 5). The importance of this site was demonstrated by the observation that alanine substitution of Cys230 resulted in a >8-fold decreased apoptotic activity (See Example 7). Furthermore, removal of the bound metal from Apo-2L by dialysis against chelating agents resulted in a 7-fold decrease in DR5 affinity and a >90-fold decrease in apoptotic activity (see Example 6). Upon removal of the Zn, the cysteines became prone to oxidation and disulfide-linked Apo-2L dimers were formed which had decreased apoptotic activity. Since the metal binding site appears to be buried in the Apo-2L trimer structure and is not expected to contact receptor, the data suggests that divalent metal ion binding may be important to maintain the trimer structure and stability of Apo-2L.

In order to map Apo-2 ligand's receptor binding site, amino acid residues important for receptor binding and biological activity were identified by alanine-scanning mutagenesis. [Cunningham et al., Science, 244:1081-1085 (1989)]. Single alanine substitutions at residues Arg149, Gln205, Val207, Tyr216, Glu236, or Tyr237 resulted in a greater than 5-fold decrease in apoptotic activity in a bioassay and showed decreased affinity for the receptors (See Examples 3 and 4). Apo-2L binding to DR4, DR5 and DcR2 was most affected by alanine substitutions at residues Gln205, Tyr216, Glu236, or Tyr237, which resulted in at least a 5-fold decreased affinity against all three receptors. All of these variants with reduced apoptotic activity also exhibited impaired binding to either DR4 or DR5 (or both) suggesting that receptor binding is required for apoptotic activity.

Alanine substitutions at residues Asp218 and Asp269 resulted in Apo-2L variants having increased apoptotic activity. (See Example 4). Residue Asp218 is located near Tyr216, which is one of the required residues for apoptotic activity. A comparison to the low resolution Apo-2L structure (114-281 form) suggests that the conformation of the 216-220 loop does not appear to be significantly altered by the presence of the D218A mutation.

When the results of the mutagenesis analysis were mapped to the Apo-2L trimer structure, the functional epitope on Apo-2L for receptor binding and biological activity was found to be located on the surface formed by the junction of two monomers (see FIG. 5), similar to TNF-beta. A shallow groove at the monomer-monomer interface forms the receptor binding site with both monomers contributing to the binding site. Residues Arg32, Tyr87, and Asp143 in TNF-alpha (corresponding to Apo-2L residues Arg158, Tyr216, and Asp267) also make contributions to TNF receptor binding. [Goh et al., Protein Engineering, 4:785-791 (1991)]. In contrast, residues of TNF-alpha (corresponding to residues Gln205, Glu236, and Tyr237 of Apo-2L) play only a minor role in TNFR binding. Thus, while for TNF-alpha the base of the trimer structure makes the most important contribution to receptor binding, in Apo-2L, important receptor binding residues are also presented on the top of the trimer structure. Apo-2L appears to be unique among the TNF family members of known structure in having a larger and more extended contact surface for interaction with its target receptors. It is believed that preferred Apo-2L variants will comprise native residues (i.e., will not be mutated) at positions corresponding to Arg149, Gln205, Val207, Tyr216, Glu236, and/or Tyr237.

The description below relates to methods of producing Apo-2 ligand by culturing host cells transformed or transfected with a vector containing Apo-2 ligand encoding nucleic acid and recovering the polypeptide from the cell culture.

The DNA encoding Apo-2 ligand may be obtained from any cDNA library prepared from tissue believed to possess the Apo-2 ligand mRNA and to express it at a detectable level. Accordingly, human Apo-2 ligand DNA can be conveniently obtained from a cDNA library prepared from human tissues, such as the bacteriophage library of human placental cDNA as described in WO97/25428. The Apo-2 ligand-encoding gene may also be obtained from a genomic library or by oligonucleotide synthesis.

Libraries can be screened with probes (such as antibodies to the Apo-2 ligand or oligonucleotides of at least about 20-80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding Apo-2 ligand is to use PCR methodology [Sambrook et al., supra; Dieffenbach et al., PCR Primer: A Laboratory Manual (Cold Spring Harbor Laboratory Press, 1995)].

Amino acid sequence fragments or variants of Apo-2 ligand can be prepared by introducing appropriate nucleotide changes into the Apo-2 ligand DNA, or by synthesis of the desired Apo-2 ligand polypeptide. Such fragments or variants represent insertions, substitutions, and/or deletions of residues within or at one or both of the ends of the intracellular region, the transmembrane region, or the extracellular region, or of the amino acid sequence shown for the full-length Apo-2 ligand in FIG. 1 (SEQ ID NO:1). Any combination of insertion, substitution, and/or deletion can be made to arrive at the final construct, provided that the final construct possesses, for instance, a desired biological activity or apoptotic activity as defined herein. In a preferred embodiment, the fragments or variants have at least about 80% amino acid sequence identity, more preferably, at least about 90% sequence identity, and even more preferably, at least 95%, 96%, 97%, 98% or 99% sequence identity with the sequences identified herein for the intracellular, transmembrane, or extracellular domains of Apo-2 ligand, or the full-length sequence for Apo-2 ligand. The amino acid changes also may alter post-translational processes of the Apo-2 ligand, such as changing the number or position of glycosylation sites or altering the membrane anchoring characteristics.

Variations in the Apo-2 ligand sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis.

Scanning amino acid analysis can be employed to identify one or more amino acids along a contiguous sequence. Among the preferred scanning amino acids are relatively small, neutral amino acids. Such amino acids include alanine, glycine, serine and cysteine. Alanine is typically a preferred scanning amino acid among this group because it eliminates the side-chain beyond the beta-carbon and is less likely to alter the main-chain conformation of the variant. [Cunningham et al., *Science*, 244:1081 (1989)]. Alanine is also typically preferred because it is the most common amino acid. Further, it is frequently found in both buried and exposed positions [Creighton, *The Proteins*, (W.H. Freeman & Co., NY); Chothia, *J. Mol. Biol.*, 150:1 (1976)].

Particular Apo-2L variants of the present invention include those Apo-2L polypeptides which include one or more of the recited alanine substitutions provided in TABLE I below. Such Apo-2L variants will typically comprise a non-naturally occurring amino acid sequence which differs from a native Apo-2L amino acid sequence (such as provided in FIG. 1; SEQ ID NO:1, for a full length or mature form of Apo-2L or an extracellular domain sequence thereof) in at least one or more amino acids. Optionally, the one or more amino acids which differ in the Apo-2L variant as compared to a native Apo-2L will comprise amino acid substitution(s) such as those indicated in Table I. Apo-2L variants of the invention include soluble Apo-2L variants comprising residues 91-281, 92-281, 95-281 or 114-281 of FIG. 1 (SEQ ID NO:1) and having one or more amino acid substitutions recited in TABLE I. Preferred Apo-2L variants will include those variants comprising residues 91-281, 92-281, 95-281 or 114-281 of FIG. 1 (SEQ ID NO:1) and having one or more amino acid substitutions recited in TABLE I which enhance biological activity, such as receptor binding.

Variations in the Apo-2 ligand sequence also included within the scope of the invention relate to amino-terminal derivatives or modified forms. Such Apo-2 ligand sequences include any of the Apo-2 ligand polypeptides described herein having a methionine or modified methionine (such as formyl methionyl or other blocked methionyl species) at the N-terminus of the polypeptide sequence.

The nucleic acid (e.g., cDNA or genomic DNA) encoding native or variant Apo-2 ligand may be inserted into a replicable vector for further cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below. Optional signal sequences, origins of replication, marker genes, enhancer elements and transcription terminator sequences that may be employed are known in the art and described in further detail in WO97/25428.

Expression and cloning vectors usually contain a promoter that is recognized by the host organism and is operably linked to the Apo-2 ligand nucleic acid sequence. Promoters are untranslated sequences located upstream (5') to the start codon of a structural gene (generally within about 100 to 1000 bp) that control the transcription and translation of a particular nucleic acid sequence, such as the Apo-2 ligand nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to Apo-2 ligand encoding DNA by removing the promoter from the source DNA by restriction enzyme digestion and inserting the isolated promoter sequence into the vector. Both the native Apo-2 ligand promoter sequence and many heterologous promoters may be used to direct amplification and/or expression of the Apo-2 ligand DNA.

Promoters suitable for use with prokaryotic and eukaryotic hosts are known in the art, and are described in further detail in WO97/25428.

A preferred method for the production of soluble Apo-2L in *E. coli* employs an inducible promoter for the regulation of product expression. The use of a controllable, inducible promoter allows for culture growth to the desirable cell density before induction of product expression and accumulation of significant amounts of product which may not be well tolerated by the host.

Three inducible promoter systems (T7 polymerase, trp and alkaline phosphatase (AP)) have been evaluated by Applicants for the expression of Apo-2L (form 114-281). The use of each of these three promoters resulted in significant amounts of soluble, biologically active Apo-2L trimer being recovered from the harvested cell paste. The AP promoter is preferred among these three inducible promoter systems tested because of tighter promoter control and the higher cell density and titers reached in harvested cell paste.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures can be used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced using standard techniques known in the art. [See, e.g., Messing et al., *Nucleic Acids Res.*, 9:309 (1981); Maxam et al., *Methods in Enzymology*, 65:499 (1980)].

Expression vectors that provide for the transient expression in mammalian cells of DNA encoding Apo-2 ligand may be employed. In general, transient expression involves the use of an expression vector that is able to replicate efficiently in a host cell, such that the host cell accumulates many copies of the expression vector and, in turn, synthesizes high levels of a desired polypeptide encoded by the expression vector [Sambrook et al., supra]. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of Apo-2 ligand that are biologically active Apo-2 ligand.

Other methods, vectors, and host cells suitable for adaptation to the synthesis of Apo-2 ligand in recombinant vertebrate cell culture are described in Gething et al., *Nature*, 293:620-625 (1981); Mantei et al., *Nature*, 281:40-46 (1979); EP 117,060; and EP 117,058.

Suitable host cells for cloning or expressing the DNA in the vectors herein include prokaryote, yeast, or higher eukaryote cells. Suitable prokaryotes for this purpose include but are not limited to eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. lichenifonnis* (e.g., *B. lichenifonnis* 41P disclosed in DD 266,710 published 12 Apr. 1989), *Pseudomonas* such as *P. aeruginosa*, and *Streptomyces*. Preferably, the host cell should secrete minimal amounts of proteolytic enzymes.

*E. coli* is the preferred host cell for use in the present invention. *E. coli* is particularly well suited for the expression of Apo-2 ligand (form 114-281), a polypeptide of under 20 kd in size with no glycosylation requirement. As a production host, *E. coli* can be cultured to relatively high cell density and is capable of producing relatively high levels of heterologous proteins.

In addition to prokaryotes, eukaryotic microbes such as filamentous fungi or yeast are suitable cloning or expression hosts for Apo-2 ligand-encoding vectors. Suitable host cells for the expression of glycosylated Apo-2 ligand are derived from multicellular organisms. Examples of all such host cells, including CHO cells, are described further in WO97/25428.

Host cells are transfected and preferably transformed with the above-described expression or cloning vectors for Apo-2 ligand production and cultured in nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, *Virology*, 52:456-457 (1978) may be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336: 348-352 (1988).

Prokaryotic cells used to produce Apo-2 ligand may be cultured in suitable culture media as described generally in Sambrook et al., supra. Particular forms of culture media that 25, may be employed for culturing *E. coli* are described further in the Examples below. Mammalian host cells used to produce Apo-2 ligand may be cultured in a variety of culture media.

Examples of commercially available culture media include Ham's F10 (Sigma), Minimal Essential Medium ("MEM", Sigma), RPMI-1640 (Sigma), and Dulbedco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: A Practical Approach*, M. Butler, ed. (IRL Press, 1991).

In accordance with the present invention, one or more divalent metal ions will typically be added to or included in the culture media for culturing or fermenting the host cells. The divalent metal ions are preferably present in or added to the culture media at a concentration level sufficient to enhance storage stability, enhance solubility, or assist in forming stable Apo-2L trimers coordinated by one or more zinc ions. The amount of divalent metal ions which may be added will be dependent, in part, on the host cell density in the culture or potential host cell sensitivity to such divalent metal ions. At higher host cell densities in the culture, it may be beneficial to increase the concentration of divalent metal ions. If the divalent metal ions are added during or after product expression by the host cells, it may be desirable to adjust or increase the divalent metal ion concentration as product expression by the host cells increases. It is generally believed that trace levels of divalent metal ions which may be present in typical commonly available cell culture media may not be sufficient for stable trimer formation. Thus, addition of further quantities of divalent metal ions, as described herein, is preferred.

The divalent metal ions are preferably added to the culture media at a concentration which does not adversely or negatively affect host cell growth, if the divalent metal ions are being added during the growth phase of the host cells in the culture. In shake flask cultures, it was observed that $ZnSO_4$ added at concentrations of greater than 1 mM can result in lower host cell density. Those skilled in the art appreciate that bacterial cells can sequester metal ions effectively by forming metal ion complexes with cellular matrices. Thus, in the cell cultures, it is preferable to add the selected divalent metal ions to the culture media after the growth phase (after the desired host cell density is achieved) or just prior to product expression by the host cells. To ensure that sufficient amounts of divalent metal ions are present, additional divalent metal ions may be added or fed to the cell culture media during the product expression phase.

The divalent metal ion concentration in the culture media should not exceed the concentration which may be detrimental or toxic to the host cells. In the methods of the invention employing the host cell, $E.\ coli$, it is preferred that the concentration of the divalent metal ion concentration in the culture media does not exceed about 1 mM (preferably, $\leq 1$ mM). Even more preferably, the divalent metal ion concentration in the culture media is about 50 micromolar to about 250 micromolar. Most preferably, the divalent metal ion used in such methods is zinc sulfate. It is desirable to add the divalent metal ions to the cell culture in an amount wherein the metal ions and Apo-2 ligand trimer can be present at a one to one molar ratio.

The divalent metal ions can be added to the cell culture in any acceptable form. For instance, a solution of the metal ion can be made using water, and the divalent metal ion solution can then be added or fed to the culture media.

In one embodiment of the invention, the selected Apo-2L (form 114-281) is expressed in $E.\ coli$, and during the culturing or fermentation of the cell culture, the process parameters are set such that cellular activities are conducted at oxygen uptake rates of approximately 1.0 to 3.0 mmoles/L-min for cultures at approximately 40-50 gm/L dry cell weight. It is preferred that the newly synthesized nascent Apo-2L polypeptides have sufficient time for proper protein folding and trimerization of Apo-2L monomers. The growth phase of the fermentation process is preferably conducted at 30° C. Just prior to the commencement of product expression; the process temperature control set-point may remain at 30° C. or be down-shifted to 25° C. for the rest of the fermentation. Optionally, it may be desired to increase cell density in the cell culture, and the above-mentioned parameters may be adjusted (or increased) accordingly. For instance, it may be advantageous to increase cell density in the cell culture to increase volumetric yield. One skilled in the art can, by using routine techniques known in the art, incrementally increase the cell density and incrementally increase the above-mentioned parameters, if desired.

Expression of the Apo-2L may be measured in a sample directly, for example, by conventional Southern blotting, Northern blotting to quantitate the transcription of mRNA [Thomas, $Proc.\ Natl.\ Acad.\ Sci.\ USA$, 77:5201-5205 (1980)], dot blotting (DNA analysis), or in situ hybridization, using an appropriately labeled probe, based on the sequences provided herein. Various labels may be employed, most commonly radioisotopes, and particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected. Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like.

Antibodies useful for immunohistochemical staining and/or assay of sample fluids may be either monoclonal or polyclonal, and may be prepared in any mammal. Conveniently, the antibodies may be prepared against a native Apo-2 ligand polypeptide or against a synthetic peptide based on the DNA sequences provided herein or against exogenous sequence fused to Apo-2 ligand DNA and encoding a specific antibody epitope.

Apo-2 ligand preferably is recovered from the culture medium as a secreted polypeptide, although it also may be recovered from host cell lysates when directly produced without a secretory signal. If the Apo-2 ligand is membrane-bound, it can be released from the membrane using a suitable detergent solution (e.g. Triton-X 100) or its extracellular region may be released by enzymatic cleavage.

When Apo-2 ligand is produced in a recombinant cell other than one of human origin, the Apo-2 ligand is free of proteins or polypeptides of human origin. However, it is usually necessary to recover or purify Apo-2 ligand from recombinant cell proteins or polypeptides to obtain preparations that are substantially homogeneous as to Apo-2 ligand. As a first step, the culture medium or lysate may be centrifuged to remove particulate cell debris. Apo-2 ligand thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE or CM; chromatofocusing; SDS-PAGE; ammonium sulfate precipitation; gel filtration using, for example, Sephadex G-75; diafiltration and protein A Sepharose columns to remove contaminants such as IgG.

In a preferred embodiment, the Apo-2 ligand can be isolated by affinity chromatography. Apo-2 ligand fragments or variants in which residues have been deleted, inserted, or substituted are recovered in the same fashion as native Apo-2 ligand, taking account of any substantial changes in properties occasioned by the variation. For example, preparation of an Apo-2 ligand fusion with another protein or polypeptide, e.g., a bacterial or viral antigen, facilitates purification; an immunoaffinity column containing antibody to the antigen can be used to adsorb the fusion polypeptide.

A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native Apo-2 ligand may require modification to account for changes in the character of Apo-2 ligand or its variants upon expression in recombinant cell culture.

During any such purification steps, it may be desirable to expose the recovered Apo-2L to a divalent metal ion-containing solution or to purification material (such as a chromatography medium or support) containing one or more divalent metal ions. In a preferred embodiment, the divalent metal ions and/or reducing agent is used during recovery or purification of the Apo-2L. Optionally, both divalent metal ions and reducing agent, such as DTT or BME, may be used during recovery or purification of the Apo-2L. It is believed that use of divalent metal ions during recovery or purification will provide for stability of Apo-2L trimer or preserve Apo-2L trimer formed during the cell culturing step.

A preferred method of recovering and purifying the expressed Apo-2L from prokaryotic host cells (most preferably from bacterial host cells) comprises the following steps: (a) extracting Apo-2L (intracellular) from $E.\ coli$ cells; (b) stabilizing the properly folded Apo-2L in a buffer solution comprising divalent metal ions and/or reducing agent; (c) purifying the Apo-2L by chromatography using, sequentially, a cationic exchanger, a hydroxyapatite and a hydrophobic interaction chromatograph, and (d) selectively eluting Apo-2L in a buffer solution comprising divalent metal ions and/or reducing agent from each such chromatographic support. The divalent metal ions and the reducing agent utilized in such methods may include a Zn sulfate, Zn chloride, Co sulfate, DTT and BME, and more preferably, a Zn sulfate or DTT. An even more detailed description of this recovery and purification process is provided in Example 8 below.

As discussed above, such methods of the invention are applicable and useful for various other proteins, besides Apo-2L, which have improved activity when in a trimerized form or which require trimerization of the protein for activity.

Formulations comprising Apo-2 ligand and one or more divalent metal ions are also provided by the present invention. It is believed that such formulations will be particularly suitable for storage (and maintain Apo-2L trimerization), as well as for therapeutic administration. Preferred formulations will comprise Apo-2L and zinc or cobalt. More preferably, the formulation will comprise an Apo-2L and zinc or cobalt solution in which the metal is at a <2× molar ratio to the protein. If an aqueous suspension is desired, the divalent metal ion in the formulation may be at a >2× molar ratio to the protein. Using zinc sulfate, Applicants have found Apo-2L (form 114-281) precipitates and forms an aqueous suspension at about a 100 mM concentration of zinc sulfate in the formulation. Those skilled in the art will appreciate that at a >2× molar ratio, there may be an upper range of concentration of the divalent metal ion in the formulation at which the metal can become deleterious to the formulation or would be undesirable as a therapeutic formulation.

The formulations may be prepared by known techniques. For instance, the Apo-2L formulation may be prepared by buffer exchange on a gel filtration column.

Typically, an appropriate amount of a pharmaceutically-acceptable salt is used in the formulation to render the formulation isotonic. Examples of pharmaceutically-acceptable carriers include saline, Ringer's solution and dextrose solution. The pH of the formulation is preferably from about 6 to about 9, and more preferably from about 7 to about 7.5. Preferably, the pH is selected so as to ensure that the zinc remains bound to the Apo-2L. If the pH is too high or too low, the zinc does not remain bound to the Apo-2L and as a result, dimers of Apo-2L will tend to form. It will be apparent to those persons skilled in the art that certain carriers may be more preferable depending upon, for instance, the route of administration and concentrations of Apo-2 ligand and divalent metal ions.

Therapeutic compositions of the Apo-2L can be prepared by mixing the desired Apo-2L molecule having the appropriate degree of purity with optional pharmaceutically acceptable carriers, excipients, or stabilizers (*Remington's Pharmaceutical Sciences,* 16th edition, Oslo, A. ed. (1980)), in the form of lyophilized formulations, aqueous solutions or aqueous suspensions.

Acceptable carriers, excipients, or stabilizers are preferably nontoxic to recipients at the dosages and concentrations employed, and include buffers such as Tris, HEPES, PIPES, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; sugars such as sucrose, mannitol, trehalose or sorbitol; salt-forming counter-ions such as sodium; and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, colloidal silica, magnesium trisilicate, polyvinyl pyrrolidone, and cellulose-based substances. Carriers for topical or gel-based forms include polysaccharides such as sodium carboxymethylcellulose or methylcellulose, polyvinylpyrrolidone, polyacrylate, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations.

Effective dosages of Apo-2 ligand in the formulations may be determined empirically, and making such determinations is within the skill in the art. It is presently believed that an effective dosage or amount of Apo-2 ligand may range from about 1 microgram/kg to about 100 mg/kg of body weight or more per day. Interspecies scaling of dosages can be performed in a manner known in the art, e.g., as disclosed in Mordenti et al., *Pharmaceut. Res.,* 8:1351 (1991). Those skilled in the art will understand that the dosage of Apo-2 ligand that must be administered will vary depending on, for example, the mammal which will receive the Apo-2 ligand, the route of administration, and other drugs or therapies being administered to the mammal.

Apo-2L to be used for in vivo administration should be sterile. This is readily accomplished by filtration through sterile filtration membranes, prior to or following lyophilization and reconstitution. Apo-2L ordinarily will be stored in lyophilized form or in solution if administered systemically. If in lyophilized form, Apo-2L is typically formulated in combination with other ingredients for reconstitution with an appropriate diluent at the time for use. An example of a liquid formulation of Apo-2L is a sterile, clear, colorless unpreserved solution filled in a single-dose vial for subcutaneous injection.

Therapeutic Apo-2L formulations generally are placed into a container having a sterile access port, for example, an intravenous solution bag or vial having a stopper pierceable by a hypodermic injection needle. The formulations are preferably administered as repeated intravenous (i.v.), subcutaneous (s.c.), intramuscular (i.m.) injections or infusions, or as aerosol formulations suitable for intranasal or intrapulmonary delivery (for intrapulmonary delivery see, e.g., EP 257, 956).

Apo-2L can also be administered in the form of sustained-release preparations. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15: 167-277 (1981) and Langer, *Chem. Tech.*, 12: 98-105 (1982) or poly(vinylalcohol)), polylactides (U.S. Pat. No. 3,773,919, EP 58,481), copolymers of L-glutamic acid and gamma ethyl-L-glutamate (Sidman et al., Biopolymers, 22: 547-556 (1983)), non-degradable ethylene-vinyl acetate (Langer et al., supra), degradable lactic acid-glycolic acid copolymers such as the Lupron Depot (injectable microspheres composed of lactic acid-glycolic acid copolymer and leuprolide acetate), and poly-D-(−)-3-hydroxybutyric acid (EP 133,988).

The Apo-2L and its formulations described herein can be employed in a variety of therapeutic and non-therapeutic applications. Among these applications are methods of treating various cancers (provided above) and viral conditions. Such therapeutic and non-therapeutic applications are described, for instance, in WO97/25428 and WO97/01633.

An article of manufacture such as a kit containing Apo-2L useful for the diagnosis or treatment of the disorders described herein comprises at least a container and a label. Suitable containers include, for example, bottles, vials, syringes, and test tubes. The containers may be formed from a variety of materials such as glass or plastic. The container holds an Apo-2L formulation that is effective for diagnosing or treating the condition and may have a sterile access port (for example, the container may be an intravenous solution bag or a vial having a stopper pierceable by a hypodermic injection needle). The label on, or associated with, the container indicates that the formulation is used for diagnosing or treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use. The article of manufacture may also comprise a second or third container with another active agent as described above.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Expression and Purification of Apo-2L Variants

Alanine substitution variants of Apo-2L were constructed by oligonucleotide-directed mutagenesis (Kunkel et al., *Proc. Natl. Acad. Sci.*, 82:488-492 (1985); Kunkel, *Methods in Enzymology*, 154:367-382 (1987)) of a plasmid (pAPOK5) (see FIG. 13), designed for the intracellular *E. coli* expression of the 91-281 amino acid form of Apo-2L under control of the trp promoter. pAPOK5 was constructed by using PCR to clone the Apo-2L cDNA (encoding residues 91-281) into plasmid pS1162 which carries the trp promoter. *E. coli* strain 294 transformed with the mutated plasmids were grown to mid-log phase at 37° C. in 250 mL M9 media plus 100 µM ZnSO$_4$, expression was induced by addition of 25 µg/mL beta-indole acrylic acid, and the cultures were grown overnight at 30° C. Cells were harvested by centrifugation and frozen.

The cell pellet was homogenized in 6 volumes 0.1 M Tris-HCl pH 8, 0.2 M NaCl, 5 mM DTT, 1 mM EDTA, and Apo-2L was isolated from the soluble fraction by IMAC on a chelating hiTRAP column (Pharmacia) charged with nickel. The Apo-2L had a weak affinity for immobilized metal and could be eluted with low concentrations of imidazole. A final purification was obtained by cation exchange chromatography on a SP hiTRAP column (Pharmacia). Concentrations of purified Apo-2L variants were determined by absorbance measurements using an e$_{280}$ of 1.4 mg$^{-1}$ ml cm$^{-1}$.

The Apo-2L variants identified by the oligonucleotide-directed mutagenesis are listed in table I.

TABLE I

Receptor binding and apoptotic activity of Apo2L variants[a]
Ratio (variant/wild-type)

| Variant | DR4-IgG K$_D$ | DR5-IgG K$_D$ | DcR2-IgG K$_D$ | Apoptosis ED$_{50}$ |
|---|---|---|---|---|
| Δzinc | 6.3 | 6.6 | 11.2 | 90.0 |
| R130A | 3 | 2.7 | 1.3 | 1.9 |
| N134A | 1.0 | 0.8 | 1.0 | 1.5 |
| L136A | 3.3 | 1.5 | 1.4 | 0.8 |
| S138A | 2.1 | 1.3 | 2.2 | 1.2 |
| N140A | 1.4 | 1.9 | 0.9 | 1.1 |
| S141A | 2.3 | 1.3 | 2.4 | 1.3 |
| K142A | 2.6 | 1.9 | 2.7 | 2.0 |
| N143A | 2.1 | 2.0 | 1.3 | 1.5 |
| R149A | 1.8 | 2.2 | 1.6 | 3.5 |
| S153A | 2.3 | 1.2 | 2.1 | 0.9 |
| E155A | 1.6 | 2 | 1.4 | 2.5 |
| R158A | 2.4 | 1.3 | 6.5 | 1.4 |
| S159A | 4.7 | 2.2 | 3.4 | 0.9 |
| R170A | 1.1 | 2.2 | 0.6 | 0.9 |
| K179A | 0.9 | 0.9 | 1.1 | 2.0 |
| R191A | 7.8 | 3.9 | 3.2 | 2.2 |
| Q193A | 1.7 | 1.1 | 1.2 | 2.2 |
| E195A | 4.6 | 1.4 | 2.6 | 0.8 |
| K197D | 2 | 2.1 | 2.9 | 1.1 |
| K201A | 4.3 | 2.7 | 10 | 2.5 |
| N202A | 2.5 | 2.5 | 1.9 | 3.2 |
| D203A | 1.5 | 1.1 | 0.6 | 0.5 |
| Q205A | 13.1 | 6.3 | 10.8 | 690 |
| V207A | 2.2 | 2.8 | 2.1 | 5.6 |
| Y213A | 1.3 | 1 | 1.5 | 1.2 |
| Y216A | 14.5 | 8.9 | 9.0 | 320 |
| D218A | 1.3 | 1.9 | 1.1 | 0.3 |
| C230S | 4.1 | 7.1 | 6.7 | 8.0 |
| E236A | 6.0 | 9.8 | 8.4 | 10.8 |
| Y237A | 7.3 | 5.0 | 48 | 8.3 |
| Y240A | 1.8 | 0.8 | 1.8 | 1.1 |
| K251A | 1.9 | 2 | 2.4 | 0.8 |
| S259A | 4.3 | 2.0 | 1.4 | 3.3 |

TABLE I-continued

Receptor binding and apoptotic activity of Apo2L variants[a]
Ratio (variant/wild-type)

| Variant | DR4-IgG $K_D$ | DR5-IgG $K_D$ | DcR2-IgG $K_D$ | Apoptosis $ED_{50}$ |
|---|---|---|---|---|
| H264A | 1.9 | 2.0 | 1.4 | 3.1 |
| D267A | 5.7 | 1.9 | 5.5 | 1.11 |
| D269A | 1.7 | 0.5 | 0.9 | 0.2 |

[a]Values shown represent the ratio of variant to wild-type. For wild-type Apo-2L (residues 91-281), the Kd values for DR4-IgG, DR5-IgG and DcR2-IgG are 0.8 ± 0.3 nM, 0.9 ± 0.4 nM, and 0.3 ± 0.2 nM. Wild-type Apo-2L (residues 91-281) gave an $ED_{50}$ of 24 ± 3.1 ng/mL in the apoptosis assay while the 114-281 form of Apo-2L was slightly more active and gave an ED50 of 16.0 ± 3.6 ng/ml. Only 2-fold changes from wild-type values are considered to be significant.

Example 2

Crystallography Analysis of Apo-2L

Crystals of Apo-2L (amino acid residues 114-281) were grown in 70 uL sitting drops containing 40 uL protein (at 2.6 mg/mL in 20 mM Tris, pH8.0), 20 uL 50 mM Tris pH 8.0, and 10 uL 8% peg 2K MME over a well solution of 50% peg 2K MME at 20° C. and were members of the spacegroup P63 with two monomer in the asymmetric unit and unit cell constants a=72.5, c=140 Angstrom and diffract to 3.9 Angstrom at room temperature. Crystals of D218A variant (see Example 1) grew in 14 uL sitting drops containing 4 uL of 4% MPD and 10 uL protein (1.7 mg/ml in 20 mM Tris pH 7.5) over a well solution of 32% MPD at 4° C. and were members of the spacegroup R32 with one monomer per asymmetric unit and unit cell parameters 66.4, c=197.7 Angstrom and diffracted to 1.3 Angstrom at −180° C. with synchroton radiation. Data sets diffracting to 3.9 Angstrom for the Apo-2L (residues 114-281) crystals and 1.9 Angstrom for the D218A variant were measured on a Rigaku rotating anode x-ray generator equipped with a MAR detector and processed with DENZO/SCALEPACK [Otwinowski et al., Proceedings of the CCP4 Study Weekend: Data Collection and Processing (eds. Sawyer et al.) pp. 56-62 Daresbury Laboratory, Daresbury, England, 1993]. A 1.3 Angstrom data set for the D218A variant was measured at the Advanced Photon Source at Argonne National Labs and was processed wtih HKL2000/SCALEPACK and had a Rsym of 6.4% (34% in the 1.35-1.30 shell), with 100% completeness and a redundancy of 12-fold, and I/<I>=12.4.

The native Apo-2L structure was solved by molecular placement using a model based on TNF-alpha (pdb code 1TNF) with the program Amore [Acta Cryst., D50:760-763 (1994)] and was refined [Brunger, X-PLOR: version 3.1, Yale Press, New Haven 1987] with strict 2-fold non-crystallographic restraints until a $R_{free}$ of 35%. This structure refined against the 1.9 Angstrom dataset until a $R_{free}$ of 25% and finally was refined against 1.3 Angstrom data with Refmac and SHELXL [Sheldrick et al., Methods in Enzymology, pp. 319-343, Academic Press, San Diego 1997] of $R_{free}$=22% and $R_{factor}$ of 20% with good geometry (rmsd bonds 0.011 Angstrom, rmsd angle 1.7°). All residues fall within the allowed regions of a Ramachandran plot. During refinement, a 28 sigma peak of electron density was observed between symmetry related Cys230 on the trimer axis. This density was modeled as a zinc ion and refined with B-factor of 10. It is believed that a chlorine molecule on the trimer axis is present as the fourth ligand to the zinc. The final model consists of residues 120-130, 142-194, 203-281 with 170 solvent molecules and one zinc ion and one chloride ion. Residues 91-119, 131-141, and 195-202 are disordered. N-terminal sequencing of several crystals confirmed that the N-terminus is intact while mass spectrometry of the starting material shows that it is full length.

A summary of the crystallographic data is provided in FIG. 2C.

Example 3

Determination of Receptor Binding Affinity of Apo-2L Variants

Dissociation constants (Kd) for binding of Apo-2L variants (see Table I) to immobilized receptor immunoadhesins were determined from surface plasmon resonance (SPR) measurements on a Pharmacia BIAcore 1000.

DR5-IgG (also referred to as Apo-2-IgG) and DcR2-IgG receptor immunoadhesins were prepared as described in WO98/51793 published Nov. 19, 1998 and WO99/10484 published Mar. 9, 1999, respectively. DR4-IgG was prepared as follows. A mature DR4 ECD sequence (amino acids 1-218; Pan et al., supra) was cloned into a pCMV-1 Flag vector (Kodak) downstream of the Flag signal sequence and fused to the CH1, hinge and Fc region of human immunoglobulin $G_1$ heavy chain as described previously [Aruffo et al., Cell, 61:1303-1313 (1990)]. The immunoadhesin was expressed by transient transfection into human 293 cells and purified from the cell supernatants by protein A affinity chromatography, as described by Ashkenazi et al., Proc. Natl. Acad. Sci., 88:10535-10539 (1991)].

The receptor immunoadhesin proteins were coupled to the sensor chip surface at a level of 1000-2000 resonance units using amine coupling chemistry (Pharmacia Biosensor). Sensorgrams were recorded for Apo-2L binding at concentrations ranging from 15.6 nM to 500 nM in 2-fold increments. The kinetics constants were determined by non-linear regression analysis and used to calculate the binding constants.

The results are shown in Table I.

Example 4

Apoptotic Activity of Apo-2L Variants In Vitro

A bioassay which measures cell viability from the metabolic conversion of a fluorescent dye was used to determine the apoptotic activity of Apo-2L variants. Serial 2-fold dilutions of Apo-2L (form 114-281) or Apo-2L variants (see Table I) were made in RPMI-1640 media (Gibco) containing 0.1% BSA, and 50 µL of each dilution was transferred to individual wells of 96-well Falcon tissue culture microplates. 50 µL of SK-MES-1 human lung carcinoma cells (ATCC HTB58) (in RMPI-1640, 0.1% BSA) were added at a density of $2 \times 10^4$ cells/well. These mixtures were incubated at 37° C. for 24 hours. At 20 hours, 25 µL of alamar Blue (AccuMed, Inc., Westlake, Ohio) was added. Cell number was determined by measuring the relative fluorescence at. 590 nm upon excitation at 530 nm. These data were analyzed by using a 4 parameter fit to calculate $ED_{50}$, the concentration of Apo-2L giving a 50% reduction in cell viability.

Single alanine substitutions at residues Arg149, Gln205, Val207, Tyr216, Glu236 or Tyr237 resulted in a greater than 5-fold decrease in apoptotic activity in the bioassay and showed decreased affinity for DR4, DR5 and DcR2 (Table I). Apo-2L binding to these receptors was most affected by alanine substitution of Gln205, Tyr216, Glu236 and Tyr237, all of which resulted in at least a 5-fold decreased affinity for all three receptors. All of the Apo-2L variants with reduced apoptotic activity also exhibited impaired binding to either DR4 or DR5 (or both) suggesting that receptor-binding is required for the biological effect. Alanine substitution of Asp218 or Asp269 resulted in a greater than 2-fold increase in apoptotic activity. It is noteworthy that most alanine substitutions have similar effects on both DR4 and DR5 binding, the only exceptions being mutation of Gln193, Glu195, Ser259, His264, and Asp267, all of which had a greater than 5-fold effect on DR4 binding (decreasing affinity) but only a small or negligible effect on DR5 binding. Changes in DcR2-binding tended to parallel the effects observed for DR4-binding. Diminished apoptotic activity appears to be most closely linked with decreased DR5-binding suggesting that DR5 is required for death signaling in SK-MES in response to Apo-2L administration.

Example 5

Elemental and Quantitative Analysis to Determine Metal Content of Apo-2L

Elemental analysis of Apo-2L was performed by using inductively coupled plasma atomic emission spectrometry (ICP-AES). For this determination, a 2 mg/mL solution of Apo-2L (residues 114-281 produced in E. coli using methods disclosed in WO97/25428; additional quantities of divalent metal ions were not added during fermentation or purification in accordance with the methods described herein) formulated in 20 mM Tris pH 7.5 was used. Levels of Cd, Co, Zn, Ni, and Cu in this sample and in a portion of the formulation buffer were determined.

TABLE II

| Sample | Cd | Co | Zn | Ni | Cu |
|---|---|---|---|---|---|
| Buffer | −0.058 | −0.090 | −0.098 | −0.098 | −0.082 |
| Apo-2L | −0.058 | 0.199 | 1.712 | −0.108 | −0.075 |

The metals bound to the Apo-2L were Zn and Co (Table II). The calculated molar ratios were 0.79 moles of Zn per mole of Apo-2L trimer and 0.06 moles of Co per mole of Apo-2L trimer. These data indicate Apo-2L has one zinc binding site per trimer. The site is 85% occupied with metal in this preparation of Apo-2L.

Example 6

Effects of Removal of Bound Zinc from Apo-2L Using Chelating Agents

A sample of Apo-2L (form 114-281) was treated with chelating agents to remove the bound zinc. The sample was first dialyzed against 2 changes of 1000 volumes each of 50 mM EDTA, then against 2 changes of 1000 volumes of 2 mM 1,10-phenanthroline, and finally against 1000 volumes of metal-free 20 mM Tris pH 7.5. The sample, before and after the chelating treatment, was assayed for receptor-binding, metal content and apoptotic activity. Receptor binding was measured as described in Example 3, metal content was determined by ICP-AES and apoptotic activity was assayed as described in Example 4. ICP-AES showed that the dialysis procedure removed the bound zinc. After this treatment, the receptor affinity was significantly reduced (Table I) and the apoptotic activity was decreased 90-fold (FIG. 4).

Circular dichroic spectra were recorded on an AVIV instrument (Lakewood, N.J.) model 202 spectropolarimeter. The spectrum was scanned from 250 to 200 nm using a step size of 0.5 nm, an averaging time of 5 seconds, and quartz rectangular cuvettes having a pathlength of 1 cm. The protein concentration was 2 μM in solutions containing PBS. As shown in FIG. 6, Apo-2L (form 114-281) gives a CD spectrum typical of a protein having a high beta-sheet content. Removal of the bound zinc results in a decreased intensity of the dichroic peaks suggesting that the beta-sheet content has been diminished.

Circular dichroism was used to monitor the effect of zinc removal on the thermal stability of Apo-2L (form 114-281). These experiments also used 1 cm quartz rectangular cuvettes and a protein concentration of 2 μM. Circular dichroism at 225 nm was monitored as the sample was heated from 30 to 100° C. Measurements were taken at 2° C. increments after allowing the sample to equilibrate at that temperature for 1 minute. Both the ellipticity (CD) and dynode voltage were recorded and the temperature dependence of the dynode voltage is plotted in FIG. 7. The dynode voltage is proportional to the absorbance of the sample. An increase in dynode voltage upon heating of the sample reflects protein aggregation. The increase in dynode voltage was concomitant with a loss of secondary structure as indicated by a decrease in the ellipticity at 225 nm. These data suggest that Apo-2L (form 114-281) aggregates upon thermal denaturation with the midpoint for this transition (Tm) occurring at about 75° C. Removal of the bound zinc results in a large decrease in the Tm for thermal denaturation to about 54° C. These data show that the bound zinc is necessary for maintenance of the structure and stability of homotrimeric Apo-2L.

Example 7

Effects of Removal of Zinc Binding Site from Apo-2L by Mutation

Cys230 of Apo-2L (form 91-281) was replaced with Ala or Ser by using oligonucleotide-directed mutagenesis as described in Example 1. The variant proteins were then expressed and purified as described in Example 1. As shown in Table I, both the C230A and C230S mutants of Apo-2L (form 91-281) had reduced receptor-binding affinity and greatly diminished apoptotic activity. Since the Apo-2L x-ray structure shows that Cys230 is a buried residue, and thus is unlikely to directly contact receptor upon complex formation, these data suggest that mutation of Cys230 indirectly affects activity by changes in the structure or stability of homotrimeric Apo-2L.

Example 8

Additions of Zn Improves Soluble Apo-2 Ligand Product Accumulation and Recovery

A. Apo-2L (Amino Acid Residues 114-281) Expression Regulated by the Alkaline Phosphatase Promoter pAPApo2-P2RU (see FIG. 12) encodes for the co-expression of Apo-2L (amino acid residues 114-281) and the tRNA's encoded by pro2 and argU. The pBR322-based plasmid [Sutcliffe, *Cold Spring Harbor Symp. Quant. Biol.*, 43:77-90 (1978)] pAPApo2-P2RU was used to produce the Apo-2L in *E. coli*. The transcriptional and translational sequences required for the expression of Apo-2L are provided by the alkaline phosphatase promoter and the trp Shine-Dalgarno, as described for the plasmid phGH1 [Chang et al., *Gene*, 55:189-196 (1987)]. The coding sequence for Apo-2L (form 114-281) is located downstream of the promoter and Shine-Dalgarno sequences and is preceded by an initiation methionine. The coding sequence includes nucleotides (shown in FIG. 1) encoding residues 114-281 of Apo-2L (FIG. 1) except that the codon encoding residue Pro119 is changed to "CCG" instead of "CCT" in order to eliminate potential secondary structure. The sequence encoding the lambda to transcriptional terminator [Scholtissek et al., *Nucleic Acids Res.*, 15:3185 (19.87)] follows the Apo-2L coding sequence. Additionally, this plasmid also includes sequences for the expression of the tRNA's pro2 [Komine et al., *J. Mol. Biol.*, 212:579-598 (1990)] and argU/dnaY [Garcia et al., *Cell*, 45:453-459 (1986)]. These genes were cloned by PCR from *E. coli* w3110 and placed downstream of the lambda to transcriptional terminator sequence. This plasmid confers both tetracycline and ampicillin resistance upon the production host.

Strain 43E7 (*E. coli* W3110 fhuA(tonA) phoA Δ(argF-lac) ptr3 degP kanS ompT ilvG+) was used as the production host for the co-expression of the Apo-2 ligand and the tRNA's. Competent cells of 43E7 were prepared and transformed with pAPApo2-P2RU using standard procedures. Transformants were picked from LB plates containing 20 μg/ml tetracycline (LB+Tet20), streak-purified, and grown in LB broth with 20 μg/ml tetracycline in a 30° C. shaker/incubator before being stored in DMSO at −80° C.

A shake flask inoculum was prepared by inoculating sterile medium using a freshly thawed stock culture vial. Appropriate antibiotics were included in the medium to provide selective pressure to ensure retention of the plasmid. The shake flask medium composition is given in Table III. Flask cultures were incubated with shaking at about 30° C. (28° C.-32° C.) for 14-18 hours. This culture was then used to inoculate the production fermentation vessel. The inoculation volume was between 0.1% and 10% of the initial volume of medium.

TABLE III

Shake Flask Medium Composition

| Ingredient | Quantity/Liter |
|---|---|
| Tetracycline | 4-20 mg |
| Tryptone | 8-12 g |
| Yeast extract | 4-6 g |
| Sodium chloride | 8-12 g |
| Sodium phosphate, added as pH7 solution | 4-6 mmol |

Production of the Apo-2L was carried out in the production medium given in Table IV. The fermentation process was conducted at about 30° C. (28-32° C.) and pH controlled at approximately 7.0 (6.5-7.5). The aeration rate and the agitation rate were set to provide adequate transfer of oxygen to the culture. At the onset of product expression, induced by phosphate depletion, the process temperature was shifted from 30° C. to 25° C. Throughout the fermentation process, the cell culture was fed glucose based on a computer algorithm to meet its carbon requirement while ensuring aerobic condition.

Two batch additions of $ZnSO_4$ were made during the fermentation process. One addition was made just prior to the induction of product expression. The second addition was made at approximately the mid-point of the production period. In this example, the additions occurred at a culture optical density of about 80-120 $OD_{550}$ and at about 28 hours post-inoculation. Sufficient amounts of 100 mM $ZnSO_4$ were added to achieve approximately 50-100 micromolar (final concentration) with each batch addition of the metal ions.

The fermentation was allowed to proceed for about 34-45 hours, after which the cell paste was harvested from the broth for subsequent product recovery evaluation.

TABLE IV

Production Medium Composition for AP Promoter Expression System

| Ingredient | Quantity/Liter |
|---|---|
| Tetracycline | 4-20 mg |
| Glucose[a] | 10-250 g |
| Ammonium sulfate[a] | 2-8 g |
| Sodium phosphate, monobasic, dihydrate[a] | 1-5 g |
| Potassium phosphate, dibasic[a] | 1-5 g |
| Potassium phosphate, monobasic[a] | 0-5 g |
| Sodium citrate, dihydrate[a] | 0.5-5 g |
| Potassium chloride | 0-5 g |
| Magnesium sulfate, heptahydrate[a] | 1.0-10 g |
| Antifoam | 0-5 ml |
| Ferric chloride, hexahydrate[a] | 20-200 mg |
| Zinc sulfate, heptahydrate[a] | 0.2-20 mg |
| Cobalt chloride, hexahydrate[a] | 0.2-20 mg |
| Sodium molybdate, dihydrate[a] | 0.2-20 mg |
| Cupric sulfate, pentahydrate[a] | 0.2-20 mg |
| Boric acid[a] | 0.2-20 mg |
| Manganese sulfate, monohydrate[a] | 0.2-20 mg |
| Casein hydrolysate[a] | 5-25 g |
| Yeast extract[a] | 5-25 g |

[a]A portion of these ingredients may be fed to the culture during the fermentation. Ammonium hydroxide was added as required to control pH.

Broth samples were taken over the time course of the fermentation process. Cells from 1 ml of broth samples diluted to a cell density of 20 $OD_{550}$ were collected by centrifugation and the resultant cell pellets were stored at −20° C. until analysis. The cell pellets were thawed and resuspended in 0.5 ml of extraction buffer (50 mM HEPES, pH 8.0, 50 mM EDTA and 0.2 mg/ml hen egg-white lysozyme) and mechanically disrupted to release the product from the cytoplasm. Solids were removed from the cell lysates by centrifugation before the clarified lysates were loaded onto a Dionex ProPac IEX HPLC column for trimer quantitation. The HPLC assay method resolves the product away from the contaminating *E. coli* proteins by use of a 5%-22% gradient of 1M NaCl in a 25 mM phosphate (pH 7.5) buffer over 25 minutes at a flow rate of 0.5 ml/min.

Frozen cell paste was thawed and resuspended in extraction buffer (100 mM Hepes buffer, pH 8.0, 50 mM EDTA, 5 mM DTT). After multiple passes of the cell suspension through a mechanical homogenizer to release the Apo-2L product from the cytoplasmic compartment, 0.2% PEI (final concentration) was added and the solids were removed by centrifugation. The clarified lysate was diluted 1:1 (v/v) with $H_2O$ and pH adjusted to 7.2 prior to loading onto the MPHS column (BioRad) pre-equilibrated with 3-4 column volumes of 50 mM Hepes/0.05% Triton/1 mM DTT pH 7.2. After a wash step with the 2-3 column volumes of equilibration buffer followed by a second wash step with 0.1M NaCl in the equilibration buffer, Apo-2L proteins were eluted off the MPHS column with 6 column volumes of a 0.1M to 0.8M NaCl gradient in the equilibration buffer. Column eluant fractions were collected, analyzed and the relevant fractions were pooled and stored @ 4-8° C.

Analysis of the Apo-2L accumulation during fermentation showed that the $ZnSO_4$ additions did not significantly affect cell growth. The production of Apo-2 ligand began when the phosphate in the medium was depleted, typically about 15-25 hours after inoculation. FIG. 8 shows the time course in the accumulation of soluble Apo-2L trimers detected by the IEX HPLC method. Cultures with ZnSO$_4$ additions had higher product concentration in the cell lysate samples than the minus-ZnSO$_4$ controls.

Analysis of the product recovery at the initial capture step (involving IEX Chromatography) (FIG. 9) shows the elution profiles of the MPHS chromatography of cell lysates from fermentations conducted in the absence and presence of ZnSO$_4$ additions. After the initial flow-through and wash steps, two main peaks, Peak A and Peak B, were resolved. By SDS-PAGE analysis, both peaks consisted of mainly Apo-2L.

Purified material from both peaks was prepared and analyzed for biological activity and stability. Results obtained from these studies suggested that Peak A was a more stable pool of Apo-2L product while Peak B had a greater tendency to aggregate over time. To minimize instability, Peak B was excluded for further recovery. The ratio of Peak A to Peak B was estimated by weighing the cut out traces representing the integrated area under each of the peaks. Results tabulated in Table V show a shift of the percent of Apo-2L as Peak A from approximately 45% on the average for the minus-ZnSO$_4$ case to approximately 80% for the plus-ZnSO$_4$ case, a significant increase in the amount of Apo-2L product in the recoverable pool.

TABLE V

| Run ID | ZnSO4 Additions | Chromatography Scale | Peak A % | Peak B % |
| --- | --- | --- | --- | --- |
| SAPO2-113 | No | 0.66 × 15.5 cm | 41.6 | 58.4 |
| LAPO2-4 | No | 4.4 × 41.5 cm | 50.4 | 49.6 |
| SAPO2-138 | Yes | 0.66 × 17.0 cm | 78.8 | 21.2 |

B. Apo-2L (Amino Acid Residues 114-281) Expression Regulated by the trp Promoter:

PS1346.Apo2L.0 Plasmid Construction: DNA encoding residues 114-281 of Apo-2L (preceded by an initiating methionine codon) was inserted into a pS1346 plasmid vector. The pS1346 plasmid is a derivative of pHGH207-1 [De-Boer et al., *Promoters: Structure and Function*, Praeger, New York, pp. 462-481 (1982)] and contains the lambda-to transcriptional terminator [Scholtissek et al., *Nucleic Acids Res.*, 15:3185 (1987)] downstream of the Apo-2L encoding sequence.

Strain 54C2 (*E. coli* W3110 fhuA(tonA) ion galE rpoHts (htpRts) clpP lacIq) was used as the production host for the expression of Apo-2 ligand (amino acid residues 114-281) where the ligand expression was regulated by the trp promoter. Competent cells of 54C2 were prepared and transformed with pS1346.Apo2L.0 using standard procedures. Transformants were picked from LB plates containing 20 µg/ml tetracycline (LB+Tet20), streak purified, and grown in LB broth with 20 µg/ml tetracycline in a 30° C. shaker/incubator before being stored in DMSO at −80° C.

Experiments conducted with the production organism, 54C2/pS1346.Apo2L.0, were performed under similar fermentation parameters as described above for the AP-promoter expression system except for minor adjustments in the medium composition (Table VI), the addition of an inducer, indole3-acrylic acid (IAA), and the length of the process. Tryptophan was added to the initial medium to repress promoter activity during the initial growth phase. The temperature shift from 30° C. to 25° C. was made when cell density of the broth reached approximately 30 OD$_{550}$. The inducer was added when the cell density of the broth reached approximately 55 OD$_{550}$. In the experiments where ZnSO$_4$ additions were made, sufficient amounts of 100 mM ZnSO$_4$ solution were added at cell density of 25 OD$_{550}$ and at 24 hours post-inoculation to achieve a final concentration of approximately 50-100 µM. Cell pastes were harvested at 6 hours post inducer addition and stored at −20° C. to −80° C.

TABLE VI

Additions to the Production Medium for AP Promoter Expression System necessary for the trp Promoter Expression System

| Ingredient | Quantity/Liter |
| --- | --- |
| L-isoleucine | 0.5-1 g |
| Tryptophan | 0.1-5 g |

Cell growth for the trp promoter system slowed after reaching 40-60 OD$_{550}$. There was significant leaky expression of Apo-2 ligand prior to induction with IAA addition and was probably responsible for the growth problem. Cell growth profiles were comparable in the absence and the presence of ZnSO$_4$ additions. FIG. 10 shows the time course in the accumulation of soluble Apo-2L trimers detected by the IEX HPLC method. The accumulation of soluble Apo-2L continued to increase in the run with ZnSO$_4$ additions and achieved a higher product concentration in the cell lysate samples.

C. Apo-2L (amino acid residues 114-281) recovery and purification from *E. coli* using divalent metal ions/DTT:

The following protocol may be employed in recovery and purification of Apo-2L from *E. coli*. First, the cells are homogenized and extraction is performed as follows. Frozen harvested *Escherichia coli* cells are suspended in 6 volumes of extraction buffer (100 mM HEPES/5 mM DTT (or 5 mM Zn sulfate instead of DTT), pH 8.0), or whole cell broth is conditioned with 5 mM DTT (or 5 mM Zn sulfate instead of DTT) @ pH 8.0. The suspension is thoroughly mixed for 1 hour at 2-8° C., then homogenized in a homogenizer (Gaulin Corporation, Everett, Mass.). The broken cell suspension is flocculated in 0.2% PEI for 1-2 hours and centrifuged by a BTPX205 (Alfa Laval Separation AB, Sweden) continuous feed centrifuge and clarified by depth filtration.

After extraction, the Apo-2L is purified as follows. Macro-Prep ceramic High S (MP-HS) chromatography is performed by conditioning the clarified cell suspension (extract) with an equal volume of H$_2$O/0.1% Triton-100 and adjusted pH to 7.2. The conditioned extract is loaded onto a column of MP-HS cation exchanger (Bio-Rad, Hercules, Calif.) that is equilibrated in 50 mM HEPES/0.05% Triton-100/1 mM DTT (or 100 uM Zn sulfate), pH 7.2. (In the preceding two steps, SP-Sepharose Fast Flow (Amersham Pharmacia, Sweden) may alternatively be employed). The non-binding proteins are flowed through and removed by washing with equilibration buffer to baseline @ A280. The column is washed with 3 column volumes of 0.1 M NaCl/equilibration buffer. The Apo-2L is eluted using a linear, 8 column-volume gradient from 0.1 to 0.8M sodium chloride in equilibration buffer. Fractions are collected and those which contain properly-folded Apo-2L, as determined by SDS-PAGE or SEC-HPLC assay, are pooled.

The pool of Apo-2L from the MP-HS column is loaded onto a column of Macro-Prep Hydroxyapatite (Bio-Rad, Hercules, Calif.) equilibrated in 50 mM HEPES/1 mM DTT (or 100 uM Zn sulfate), pH 7.2. (As an alternative to the Macro-Prep Hydroxyapatite, SP-Sepharose Fast Flow may be employed). After the sample is loaded, the column is washed with equilibration buffer to baseline @ A280. The Apo-2L is eluted out of the column by using an isocratic step of 0.15 M sodium phosphate in equilibration buffer.

The pool of MP-HA is conditioned with an equal volume of 1.0 M Ammonium Sulfate/50 mM Tris/1 mM DTT (or 100 uM Zn sulfate), pH 7.5, and then loaded onto a column of Phenyl-Sepharose FF (Amersham Pharmacia, Sweden) that is equilibrated in 0.5 M Ammonium sulfate/50 mM Tris/1 mM DTT (or 100 uM Zn sulfate), pH 7.5. (As an alternative to the 0.5M ammonium sulfate, 0.6M sodium sulfate may be employed). The column is washed with equilibration buffer, and the Apo-2L is collected in the column effluent.

The Apo-2L is then formulated by ultrafiltration and G-25 Gel Filtration (Amersham Pharmacia, Sweden) chromatography. The pool of phenyl-Sepharose is concentrated with TFF Ultrafiltration (Millipore, Bedford, Mass.) and formulated on a G-25 gel filtration column with 20 mM Tris/8% Trehalose, pH 7.5. (As an alternative, the material may be formulated by diafiltration). The final purity of Apo-2L can be determined by SDS-PAGE, SEC-HPLC and Amino Acid sequence analysis.

Example 9

Additions of Cobalt Chloride Improve Soluble Apo-2 Ligand Product Accumulation and Recovery Apo-2L (Amino Acid Residues 114-281) Expression Regulated by the Alkaline Phosphatase Promoter The same production organism, medium composition, fermentation conditions and sample analysis described in Example 8A were used in studying the effect of additions of metal ion other than Zn, namely cobalt chloride, on Apo-2L (amino acid residues 114-281) product accumulation. A solution of 100 mM $CoCl_2$ in $H_2O$ was used in place of the 100 mM $ZnSO_4$ and sufficient amounts were added to arrive at a final concentration of 50-100 μM at each of the two additions.

FIG. 11 shows the benefits of additions of $CoCl_2$ on soluble Apo-2L accumulation during the fermentation process. Like the $ZnSO_4$ addition experiments, though not as significant, a higher accumulation rate of soluble Apo-2L product was detected by the IEX HPLC assay method. The data demonstrates that additions of certain metal ions generally improve soluble Apo-2L accumulation, likely as a result of their ability to stabilize the assembled trimers of Apo-2L.

Example 10

Effects of Various Metal Ions on Apo-2L Formulations

In vitro assays were conducted by incubating 50 μl Apo-2L (form 114-281) at 5° C. for 24 hours with 5 mM of metal salt (each of which are recited in Table VII below; 100:1 molar ratio of metal to protein) in a 20 mM Tris, 8% trehalose, 0.01% Tween 20, pH 7.5 formulation. The samples were then evaluated for apoptotic activity using a SK-MES assay as described in Example 4.

The EC50 (or Apo-2L concentration that results in killing of 50% of the cells) is shown in Table VII (units of ng/ml). As shown in Table VII, addition of Zn acetate and Zn sulfate to the culture enhanced Apo-2L activity.

TABLE VII

| Metal Added | Bioassay EC50 |
| --- | --- |
| Control | 19.0 ± 1.9 (n = 3) |
| Mn acetate | 19.8 |
| Mn chloride | 19.9 |

TABLE VII-continued

| Metal Added | Bioassay EC50 |
| --- | --- |
| Fe acetate | 32.5 |
| Co acetate | 25.9 |
| Co chloride | 17.9 |
| Co sulfate | 16.7 |
| Ni acetate | 18.7 |
| Cu acetate | 844 |
| Cu chloride | 984 |
| Cu sulfate | 774 |
| Ag acetate | 20 |
| Zn acetate | 12.3 |
| Zn chloride | 17.2 |
| Zn sulfate | |
| (100:1) | 9.3 ± 1.2 (n = 3) |
| (10:1) | 10.0 ± 0 (n = 2) |
| (1:1) | 11.5 ± 0.7 (n = 2) |

Example 11

Effects of Zinc Metal Ions on Apo-2 Ligand Formulation Stability

As indicated in Example 8B, the first, step in the purification process using MPHS cation exchanger gives two peaks, A and B. To investigate the storage stability of the two peaks, Apo-2L (form 114-281) was extracted from the *E. coli* expressed product (using the pS1346.ApoL.0 plasmid with trp promoter), and purified by MPHS cation exchanger. The MPHS Peak A was further purified by MP-Hydroxyapatite and Phenyl-Sepharose FF, and then formulated using G-25 gel filtration. The MPHS Peak B was purified by MP-Hydroxyapatite, Phenyl-Sepharose FF, and Ni-NTA Superflow and then formulated on G-25 gel filtration into 20 mM Tris, 8% trehalose, 0.01% Tween 20, pH 7.5. The samples were sterile filled into 3 cc glass vials and sealed with teflon coated greybutyl stoppers. The storage stability of the purified and formulated Peaks A and B were evaluated at the time (weeks ("wk") or months ("mo")) and temperatures (° C.) listed in Table VIII.

TABLE VIII

| | SDS-SEC % M | SDS-SEC % D | SEC % recovery | SEC % trimer | RP % main | EC50 |
| --- | --- | --- | --- | --- | --- | --- |
| Peak A | | | | | | |
| 1 wk, −70 C. | ND | ND | | 98.60 | 78.10 | |
| 1 wk, 37 C. | ND | ND | 96.7 | 98.2 | 73.60 | |
| 2 mo, −70 C. | 88.85 | 7.50 | | 93.93 | 74.52 | |
| 2 mo, 30 C. | 84.90 | 10.58 | 65.07 | 94.03 | 53.98 | |
| 6 mo, −70 C. | 93.00 | 5.80 | | | ND | 11.1 |
| 6 mo, 5 C. | 87.00 | 9.44 | 100 | | ND | 14.8 |
| 6 mo, 30 C. | 80.00 | 8.68 | 76 | | ND | 67.8 |
| Peak B | | | | | | |
| 1 wk, −70 C. | ND | ND | | 98.70 | 75.3 | |
| 1 wk, 37 C. | ND | ND | 101.1 | 98.3 | 61.4 | |
| 2 mo, −70 C. | 94.03 | 3.79 | | 90.00 | 65.77 | |

TABLE VIII-continued

| | SDS-SEC % M | SDS-SEC % D | SEC % recovery | SEC % trimer | RP % main | EC50 |
|---|---|---|---|---|---|---|
| 2 mo, 30 C. | 94.12 | 4.54 | 46.07 | 94.12 | 32.185 | |
| 6 mo, −70 C. | 82.00 | 11.25 | | | ND | 10.3 |
| 6 mo, 5 C. | 73.50 | 17.00 | 92 | | ND | 12.6 |
| 6 mo, 30 C. | 47.00 | 23.20 | 38 | | ND | Dead |

Table VIII shows, among other things, the percent monomer (% M) and percent dimer (% D); "ND" refers to those values not determined. Peak A included slightly less dimer and other impurities than Peak B at Day 0. As shown in Table VIII, Peak B was found to be more thermally labile, as assessed by the more extensive precipitation at 30° C. (approximately 40% more at the 2 month point). Even at 5° C., Peak B was approximately 2-fold more prone to dimer formation than Peak A. Biochemical analysis of Peaks A and B indicated that the material of each was biochemically equivalent except for their respective stability properties. It is believed that the lower stability of Peak B may be related to improper (trimer) assembly or lower zinc content (0.83 molar ratio of Zinc to protein for Peak A and 0.7 molar ratio of Zinc to protein for Peak B).

What is claimed is:

1. A method of making Apo-2 ligand, comprising the steps of: (a) providing an *E. Coli* host cell comprising a replicable vector containing a nucleotide sequence encoding Apo-2 ligand polypeptide; (b) providing culture media containing zinc at a concentration of about 50 micromolar to about 250 micromolar; (c) culturing the host cell in the culture media under conditions sufficient to express the Apo-2 ligand; and (d) recovering the Apo-2 ligand from the host cell or culture media, wherein the Apo-2 ligand comprises a polypeptide selected from the group consisting of:
(i) a polypeptide having amino acid residues 1 to 281 of FIG. 1 (SEQ ID NO:1);
(ii) a polypeptide having amino acid residues 114 to 281 of FIG. 1 (SEQ ID NO:1);
(iii) a fragment of the polypeptide of (i) or (ii) which induces apoptosis in at least one type of mammalian cell or binds an Apo-2 ligand receptor; and
(iv) a polypeptide having at least 80% identity to the polypeptide of (i) or (ii), and induces apoptosis in at least one type of mammalian cell or binds an Apo-2 ligand receptor.

2. The method of claim 1 wherein said zinc comprises zinc sulfate.

3. The method of claim 1 wherein said replicable vector comprises a nucleotide sequence encoding one or more tRNA molecules.

4. The method of claim 3 wherein said replicable vector is the pAPApo2-P2RU vector.

5. The method of claim 1 wherein said Apo-2 ligand comprises amino acids 114 to 281 of FIG. 1 (SEQ ID NO:1).

6. The method of claim 1 wherein said Apo-2 ligand comprises amino acids 1 to 281 of FIG. 1 (SEQ ID NO:1) or a fragment thereof which induces apoptosis in at least one type of mammalian cell.

7. The method of claim 1, wherein in step (d), the Apo-2 ligand is recovered from the host cell or culture media in the presence of a reducing agent.

8. The method of claim 7, wherein said reducing agent is selected from the group consisting of DTT and BME.

* * * * *

```
                         SEQUENCE LISTING

<160> NUMBER OF SEQ ID NOS: 7

<210> SEQ ID NO 1
<211> LENGTH: 281
<212> TYPE: PRT
<213> ORGANISM: Homo sapiens

<400> SEQUENCE: 1

Met Ala Met Met Glu Val Gln Gly Gly Pro Ser Leu Gly Gln Thr
  1               5                  10                  15

Cys Val Leu Ile Val Ile Phe Thr Val Leu Leu Gln Ser Leu Cys
                 20                  25                  30

Val Ala Val Thr Tyr Val Tyr Phe Thr Asn Glu Leu Lys Gln Met
                 35                  40                  45

Gln Asp Lys Tyr Ser Lys Ser Gly Ile Ala Cys Phe Leu Lys Glu
                 50                  55                  60

Asp Asp Ser Tyr Trp Asp Pro Asn Asp Glu Glu Ser Met Asn Ser
                 65                  70                  75

Pro Cys Trp Gln Val Lys Trp Gln Leu Arg Gln Leu Val Arg Lys
                 80                  85                  90

Met Ile Leu Arg Thr Ser Glu Glu Thr Ile Ser Thr Val Gln Glu
                 95                 100                 105

Lys Gln Gln Asn Ile Ser Pro Leu Val Arg Glu Arg Gly Pro Gln
                110                 115                 120

Arg Val Ala Ala His Ile Thr Gly Thr Arg Gly Arg Ser Asn Thr
                125                 130                 135

Leu Ser Ser Pro Asn Ser Lys Asn Glu Lys Ala Leu Gly Arg Lys
                140                 145                 150

Ile Asn Ser Trp Glu Ser Ser Arg Ser Gly His Ser Phe Leu Ser
                155                 160                 165

Asn Leu His Leu Arg Asn Gly Glu Leu Val Ile His Glu Lys Gly
                170                 175                 180

Phe Tyr Tyr Ile Tyr Ser Gln Thr Tyr Phe Arg Phe Gln Glu Glu
                185                 190                 195

Ile Lys Glu Asn Thr Lys Asn Asp Lys Gln Met Val Gln Tyr Ile
                200                 205                 210

Tyr Lys Tyr Thr Ser Tyr Pro Asp Pro Ile Leu Leu Met Lys Ser
                215                 220                 225

Ala Arg Asn Ser Cys Trp Ser Lys Asp Ala Glu Tyr Gly Leu Tyr
                230                 235                 240
```

```
Ser Ile Tyr Gln Gly Gly Ile Phe Glu Leu Lys Glu Asn Asp Arg
            245                 250                 255

Ile Phe Val Ser Val Thr Asn Glu His Leu Ile Asp Met Asp His
            260                 265                 270

Glu Ala Ser Phe Phe Gly Ala Phe Leu Val Gly
            275                 280

<210> SEQ ID NO 2
<211> LENGTH: 1042
<212> TYPE: DNA
<213> ORGANISM: Homo sapiens
<220> FEATURE:
<221> NAME/KEY: VARIATION
<222> LOCATION: 447
<223> OTHER INFORMATION: N CAN BE T OR G

<400> SEQUENCE: 2
tttcctcact gactataaaa gaatagagaa ggaagggctt cagtgaccgg         50
ctgcctggct gacttacagc agtcagactc tgacaggatc atggctatga        100
tggaggtcca gggggaccc agcctgggac agacctgcgt gctgatcgtg         150
atcttcacag tgctcctgca gtctctctgt gtggctgtaa cttacgtgta        200
ctttaccaac gagctgaagc agatgcagga caagtactcc aaaagtggca        250
ttgcttgttt cttaaaagaa gatgacagtt attgggaccc caatgacgaa        300
gagagtatga cagcccctg ctggcaagtc aagtggcaac tccgtcagct         350
cgttagaaag atgattttga aacctctga ggaaaccatt tctacagttc         400
aagaaaagca acaaaatatt tctcccctag tgagagaaag aggtccncag        450
agagtagcag ctcacataac tgggaccaga ggaagaagca acacattgtc        500
ttctccaaac tccaagaatg aaaaggctct gggccgcaaa ataaactcct        550
gggaatcatc aaggagtggg cattcattcc tgagcaactt gcacttgagg        600
aatggtgaac tggtcatcca tgaaaaaggg ttttactaca tctattccca        650
aacatacttt cgatttcagg aggaaataaa agaaaacaca aagaacgaca        700
aacaaatggt ccaatatatt tacaaataca caagttatcc tgaccctata        750
ttgttgatga aaagtgctag aaatagttgt tggtctaaag atgcagaata        800
tggactctat tccatctatc aagggggaat atttgagctt aaggaaaatg        850
acagaatttt tgtttctgta acaaatgagc acttgataga catggaccat        900
gaagccagtt ttttcggggc cttttagtt ggctaactga cctggaaaga        950
aaaagcaata acctcaaagt gactattcag ttttcaggat gatacactat       1000
gaagatgttt caaaaatct gaccaaaaca acaaacaga aa                1042

<210> SEQ ID NO 3
<211> LENGTH: 144
<212> TYPE: PRT
<213> ORGANISM: Homo sapiens

<400> SEQUENCE: 3

Lys Pro Ala Ala His Leu Ile Gly Asp Pro Ser Lys Gln Asn Ser
  1               5                  10                  15

Leu Leu Trp Arg Ala Asn Thr Asp Arg Ala Phe Leu Gln Asp Gly
             20                  25                  30

Phe Ser Leu Ser Asn Asn Ser Leu Leu Val Pro Thr Ser Gly Ile
```

```
                    35                  40                  45
Tyr Phe Val Tyr Ser Gln Val Val Phe Ser Gly Lys Ala Tyr Ser
                50                  55                  60

Pro Lys Ala Thr Ser Ser Pro Leu Tyr Leu Ala His Glu Val Gln
                65                  70                  75

Leu Phe Ser Ser Gln Tyr Pro Phe His Val Pro Leu Leu Ser Ser
                80                  85                  90

Gln Lys Met Val Tyr Pro Gly Leu Gln Glu Pro Trp Leu His Ser
                95                 100                 105

Met Tyr His Gly Ala Ala Phe Gln Leu Thr Gln Gly Asp Gln Leu
               110                 115                 120

Ser Thr His Thr Asp Gly Ile Pro His Leu Val Leu Ser Pro Ser
               125                 130                 135

Thr Val Phe Phe Gly Ala Phe Ala Leu
               140

<210> SEQ ID NO 4
<211> LENGTH: 147
<212> TYPE: PRT
<213> ORGANISM: Homo sapiens

<400> SEQUENCE: 4

Lys Pro Val Ala His Val Val Ala Asn Pro Gln Ala Glu Gly Gln
  1               5                  10                  15

Leu Gln Trp Leu Asn Arg Arg Ala Asn Ala Leu Leu Ala Asn Gly
                 20                  25                  30

Val Glu Leu Arg Asp Asn Gln Leu Val Val Pro Ser Glu Gly Leu
                 35                  40                  45

Tyr Leu Ile Tyr Ser Gln Val Leu Phe Lys Gly Gln Gly Cys Pro
                 50                  55                  60

Ser Thr His Val Leu Leu Thr His Thr Ile Ser Arg Ile Ala Val
                 65                  70                  75

Ser Tyr Gln Thr Lys Val Asn Leu Leu Ser Ala Ile Lys Ser Pro
                 80                  85                  90

Cys Gln Arg Glu Thr Pro Glu Gly Ala Glu Ala Lys Pro Trp Tyr
                 95                 100                 105

Glu Pro Ile Tyr Leu Gly Gly Val Phe Gln Leu Glu Lys Gly Asp
                110                 115                 120

Arg Leu Ser Ala Glu Ile Asn Arg Pro Asp Tyr Leu Asp Phe Ala
                125                 130                 135

Glu Ser Gly Gln Val Tyr Phe Gly Ile Ile Ala Leu
                140                 145

<210> SEQ ID NO 5
<211> LENGTH: 141
<212> TYPE: PRT
<213> ORGANISM: Homo sapiens

<400> SEQUENCE: 5

Gln Ile Ala Ala His Val Ile Ser Glu Ala Ser Ser Lys Thr Thr
  1               5                  10                  15

Ser Val Leu Gln Trp Ala Glu Lys Gly Tyr Tyr Thr Met Ser Asn
                 20                  25                  30

Asn Leu Val Thr Leu Glu Asn Gly Lys Gln Leu Thr Val Lys Arg
                 35                  40                  45

Gln Gly Leu Tyr Tyr Ile Tyr Ala Gln Val Thr Phe Cys Ser Asn
```

```
                    50                  55                  60
Arg Glu Ala Ser Ser Gln Ala Pro Phe Ile Ala Ser Leu Cys Leu
                65                  70                  75
Lys Ser Pro Gly Arg Phe Glu Arg Ile Leu Leu Arg Ala Ala Asn
            80                  85                  90
Thr His Ser Ser Ala Lys Pro Cys Gly Gln Gln Ser Ile His Leu
        95                  100                 105
Gly Gly Val Phe Glu Leu Gln Pro Gly Ala Ser Val Phe Val Asn
    110                 115                 120
Val Thr Asp Pro Ser Gln Val Ser His Gly Thr Gly Phe Thr Ser
        125                 130                 135
Phe Gly Leu Leu Lys Leu
            140

<210> SEQ ID NO 6
<211> LENGTH: 137
<212> TYPE: PRT
<213> ORGANISM: Homo sapiens

<400> SEQUENCE: 6

Arg Lys Val Ala His Leu Thr Gly Lys Ser Asn Ser Arg Ser Met
 1               5                  10                  15
Pro Leu Glu Trp Glu Asp Thr Tyr Gly Ile Val Leu Leu Ser Gly
                20                  25                  30
Val Lys Tyr Lys Lys Gly Gly Leu Val Ile Asn Glu Thr Gly Leu
            35                  40                  45
Tyr Phe Val Tyr Ser Lys Val Tyr Phe Arg Gly Gln Ser Cys Asn
        50                  55                  60
Asn Leu Pro Leu Ser His Lys Val Tyr Met Arg Asn Ser Lys Tyr
    65                  70                  75
Pro Gln Asp Leu Val Met Met Glu Gly Lys Met Met Ser Tyr Cys
            80                  85                  90
Thr Thr Gly Gln Met Trp Ala Arg Ser Ser Tyr Leu Gly Ala Val
        95                  100                 105
Phe Asn Leu Thr Ser Ala Asp His Leu Tyr Val Asn Val Ser Glu
    110                 115                 120
Leu Ser Leu Val Asn Phe Glu Glu Ser Gln Thr Phe Phe Gly Leu
            125                 130                 135
Tyr Lys

<210> SEQ ID NO 7
<211> LENGTH: 152
<212> TYPE: PRT
<213> ORGANISM: Homo sapiens

<400> SEQUENCE: 7

Gln Pro Phe Ala His Leu Thr Ile Asn Ala Thr Asp Ile Pro Ser
 1               5                  10                  15
Gly Ser His Lys Val Ser Leu Ser Ser Trp Tyr His Asp Arg Gly
                20                  25                  30
Trp Ala Lys Ile Ser Asn Met Thr Phe Ser Asn Gly Lys Leu Ile
            35                  40                  45
Val Asn Gln Asp Gly Phe Tyr Tyr Leu Tyr Ala Asn Ile Cys Phe
        50                  55                  60
Arg His His Glu Thr Ser Gly Asp Leu Ala Thr Glu Tyr Leu Gln
    65                  70                  75
```

```
Leu Met Val Tyr Val Thr Lys Thr Ser Ile Lys Ile Pro Ser Ser
                80              85              90

His Thr Leu Met Lys Gly Gly Ser Thr Lys Tyr Trp Ser Gly Asn
                95              100             105

Ser Glu Phe His Phe Tyr Ser Ile Asn Val Gly Gly Phe Phe Lys
                110             115             120

Leu Arg Ser Gly Glu Glu Ile Ser Ile Glu Val Ser Asn Pro Ser
                125             130             135

Leu Leu Asp Pro Asp Gln Asp Ala Thr Tyr Phe Gly Ala Phe Lys
                140             145             150

Val Arg
```